United States Patent [19]

Brunner

[11] Patent Number: 4,995,902
[45] Date of Patent: Feb. 26, 1991

[54] NOVEL HERBICIDES

[75] Inventor: Hans-Georg Brunner, Lausen, Switzerland

[73] Assignee: Ciba-Geigy Corporation, Ardsley, N.Y.

[21] Appl. No.: 378,119

[22] Filed: Jul. 11, 1989

[30] Foreign Application Priority Data

Jul. 25, 1988 [CH] Switzerland .................. 2825/88
Jan. 5, 1989 [CH] Switzerland ..................... 29/89

[51] Int. Cl.⁵ ............... C07D 213/50; A01N 43/40
[52] U.S. Cl. .................................. 71/94; 546/314; 546/315; 546/327; 47/57.6
[58] Field of Search ............... 546/314, 315; 71/94

[56] References Cited

U.S. PATENT DOCUMENTS

| 4,319,916 | 3/1982 | Abdulla | 71/94 |
| 4,631,081 | 12/1986 | Watson et al. | 71/94 |
| 4,708,732 | 11/1987 | Carter | 71/92 |
| 4,781,751 | 11/1988 | Chin | 71/103 |
| 4,783,213 | 11/1988 | Lee | 71/90 |
| 4,872,902 | 10/1987 | Brunner | 71/105 |

FOREIGN PATENT DOCUMENTS

| 0090262 | 3/1983 | European Pat. Off. |
| 0283152 | 2/1988 | European Pat. Off. |
| 283261 | 9/1988 | European Pat. Off. |
| 0317158 | 11/1988 | European Pat. Off. |
| 316491 | 5/1989 | European Pat. Off. |
| 2206114 | 6/1988 | United Kingdom |

OTHER PUBLICATIONS

193087D CA vol. 83, 1975.

Primary Examiner—Jane T. Fan
Attorney, Agent, or Firm—Kevin T. Mansfield; Edward McC.Roberts

[57] ABSTRACT

The invention relates to novel herbicidally active cyclohexanediones of formula I or I'

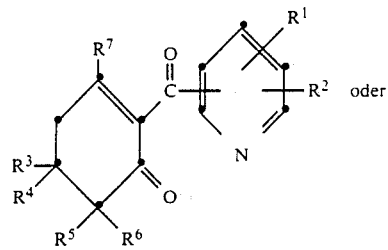

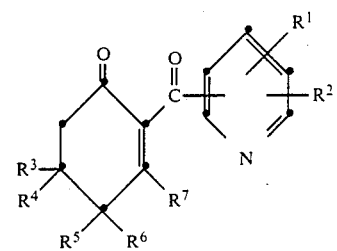

in which $R^1$ and $R^2$ independently of one another are each hydrogen; halogen; nitro; cyano; $C_1$-$C_4$alkyl; $C_1$-$C_4$alkoxy; $C_1$-$C_4$alkyl-$S(O)_n$—; $COR^8$; $C_1$-$C_4$haloalkoxy; or $C_1$-$C_4$haloalkyl; $R^3$, $R^4$ and $R^5$ independently of one another are each hydrogen; $C_1$-$C_4$alkyl; or phenyl or benzyl each unsubstituted or substituted by up to three identical or different substituents from halogen, nitro, cyano, $C_1$-$C_4$alkyl, $C_1$-$C_4$alkoxy, $C_1$-$C_4$alkyl-$S(O)_n$—, $C_1$-$C_4$haloalkyl, $C_1$-$C_4$haloalkyl-$S(O)_n$— and $C_1$-$C_4$haloalkoxy; $R^6$ is hydrogen; $C_1$-$C_4$alkyl, $C_1$-$C_4$alkoxycarbonyl; or cyano; $R^7$ is OH; or $O^{\ominus}M^{\oplus}$; $R^8$ is OH; $C_1$-$C_4$alkoxy; $NH_2$; $C_1$-$C_4$alkylamino; or di-$C_1$-$C_4$alkylamino; n is 0, 1 or 2; M+ is a cation equivalent of a metal ion or of an ammonium ion that is unsubstituted or substituted by up to three $C_1$-$C_4$alkyl, $C_1$-$C_4$hydroxyalkyl or $C_1$-$C_4$alkoxy-$C_1$-$C_4$alkyl groups, to herbicidal compositions, to processes for the preparation of novel compounds and to novel intermediates and the preparation thereof.

15 Claims, No Drawings

NOVEL HERBICIDES

The present invention relates to novel cyclohexanediones having herbicidal activity, to agrochemical compositions containing those cyclohexanediones, to the use thereof for controlling undesired plant growth and to processes for the preparation of the compounds of the invention. The invention also relates to novel intermediates and to processes for the preparation thereof.

Numerous substituted cyclohexane-1,3-diones having herbicidal activity are already known. These compounds are not always satisfactory in terms of strength of activity, duration of activity, selectivity and applicability. It has surprisingly been found that, in contrast to these known compounds, the novel cyclohexane-1,3-diones of the general formula I and I' have good herbicidal activity.

The invention relates to the novel cyclohexane-1,3-diones of formula I or I'

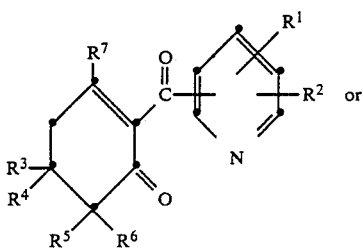

or

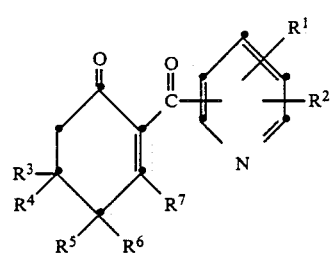

in which $R^1$ and $R^2$ independently of one another are each hydrogen; halogen; nitro; cyano; $C_1$–$C_4$alkyl; $C_1$–$C_4$alkoxy; $C_1$–$C_4$alkyl—S(O)n–; $COR^8$; $C_1$–$C_4$haloalkoxy; or $C_1$–$C_4$haloalkyl; $R^3$, $R^4$ and $R^5$ independently of one another are each hydrogen; $C_1$–$C_4$alkyl; or phenyl or benzyl each unsubstituted or substituted by up to three identical or different substituents from halogen, nitro, cyano, $C_1$–$C_4$alkyl, $C_1$–$C_4$alkoxy, $C_1$–$C_4$alkyl-S(O)n—, $C_1$–$C_4$haloalkyl, $C_1$–$C_4$haloalkyl-S(O)$_n$— and $C_1$–$C_4$haloalkoxy; $R^6$ is hydrogen; $C_1$–$C_4$alkyl; $C_1$–$C_4$alkoxycarbonyl; or cyano; $R^7$ is OH; or $O^\ominus M^\oplus$; $R^8$ is OH; $C_1$–$C_4$alkoxy; $NH_2$; $C_1$–$C_4$alkylamino; or di-$C_1$–$C_4$alkylamino; n is 0, 1 or 2; $M^\oplus$ is a cation equivalent of a metal ion or of an ammonium ion that is unsubstituted or substituted by up to three $C_1$–$C_4$alkyl, $C_1$–$C_4$hydroxyalkyl or $C_1$–$C_4$alkoxy-$C_1C_4$alkyl groups.

In the definitions used in this description, the generic terms used, and the substituents obtainable by combining individual sub-terms, include, for example, the following specific individual substituents, but this list does not imply any limitation of the invention.

Alkyl: methyl, ethyl, n-propyl, isopropyl, n-butyl, sec.-butyl, isobutyl and tert.-butyl; preferably methyl, ethyl and isopropyl.

Halogen: fluorine, chlorine, bromine and iodine; preferably fluorine, chlorine and bromine; especially preferably (for R: and R ) fluorine and chlorine and bromine.

Haloalkyl: fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl; preferably trichloromethyl, difluorochloromethyl and dichlorofluoromethyl. Alkoxy: methoxy, ethoxy, propoxy, isopropoxy, n-butoxy, iso-butoxy, sec.-butoxy and tert.-butoxy; preferably methoxy.

Haloalkoxy: fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy; preferably difluoromethoxy, 2-chloroethoxy and trifluoromethoxy.

Alkoxycarbonyl: methoxycarbonyl, ethoxycarbonyl, 4-propoxycarbonyl, isopropoxycarbonyl and n-butoxycarbonyl; preferably methoxycarbonyl and ethoxycarbonyl.

Alkylthio: methylthio, ethylthio, propylthio, isopropylthio, n-butylthio, isobutylthio, sec.-butylthio or tert.-butylthio; preferably methylthio and ethylthio.

Alkylsulfinyl: methylsulfinyl, ethylsulfinyl, n-propylsulfinyl, isopropylsulfinyl, n-butylsulfinyl, sec.-butylsulfinyl, isobutylsulfinyl; preferably methylsulfinyl and ethylsulfinyl.

Alkylsulfonyl: methylsulfonyl, ethylsulfonyl, n-propylsulfonyl, isopropylsulfonyl, n-butylsulfonyl, sec.-butylsulfonyl, isobutylsulfonyl; preferably methyl- and ethyl-sulfonyl.

In view of their chemical structure, the compounds of formula I can be regarded as 1,3-cyclohexanediones acylated in the 2-position. Numerous tautomeric forms can be derived from this basic structure. The invention includes all tautomers.

The individual meanings of the substituents $R^1$ to $R^7$, which are separated from each other by semi-colons, are to be regarded as sub-groups of those substituents. The invention includes also the definitions of compounds of formula I that can be obtained by deleting one or more of those subgroups.

The compounds of formula I and I' exist in an equilibrium of the two forms according to the following equation:

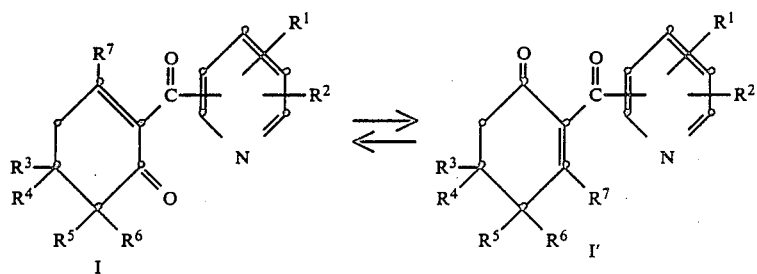

In the case of the hydroxy compounds ($R^7$=OH), apart from the three enol forms Ia, Ia''' and Ia', the triketo form Ia'' may occur in accordance with the following tautomeric equilibrium:

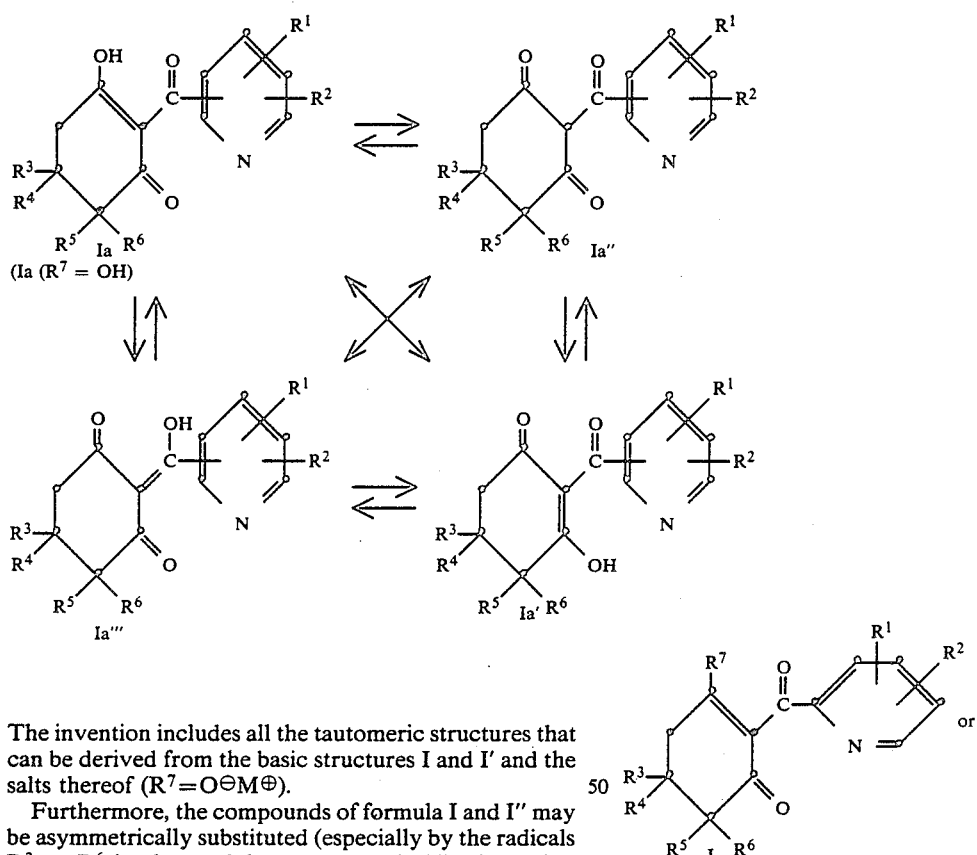

The invention includes all the tautomeric structures that can be derived from the basic structures I and I' and the salts thereof ($R^7$=O$^\ominus$M$^\oplus$).

Furthermore, the compounds of formula I and I'' may be asymmetrically substituted (especially by the radicals $R^3$ to $R^6$ in the cyclohexane system). The invention includes both the racemate and the enriched and optically pure forms of the respective stereoisomers.

The asymmetrically substituted compounds of formula I are generally obtained in the form of racemates in the processes described in this application, provided chiral educts are not used. The stereoisomers can thus be resolved according to methods that are known per se, such as, for example, by fractional crystallisation after salt formation with optically pure bases, acids or meal complexes, or by chromatographic processes on the basis of the physicochemical properties.

Both the racemate and the stereoisomeric forms are included in the present invention.

Attention is drawn to the compounds of formula I or I'

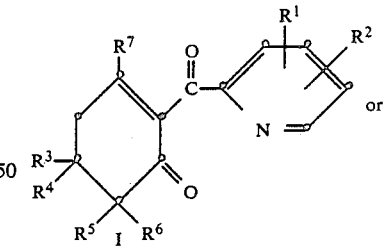

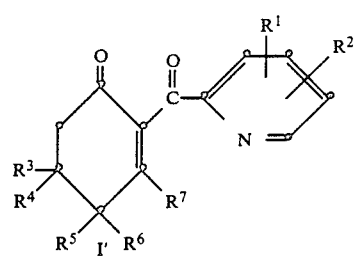

in which the pyridinecarbonyl radical is bonded by way of the 2-position of the pyridine system.

Attention is drawn also to the compounds of formula I or I'

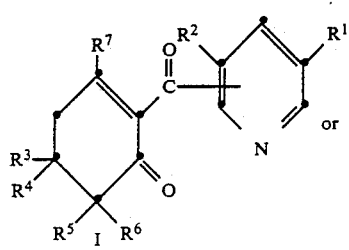

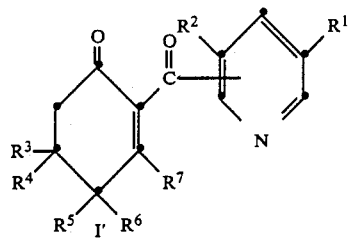

in which the radicals $R^1$ and $R^2$ are bonded in the 3- and 5-positions of the pyridine system.

Compounds of formula I or I′

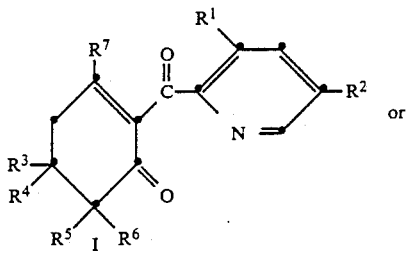

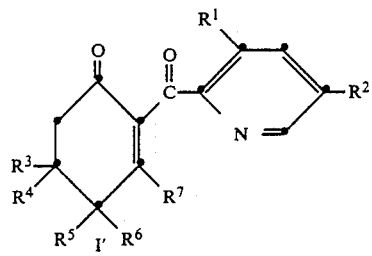

in which the radicals $R^1$ and $R^2$ are bonded in the 3- and 5-positions of the pyridine ring and the pyridinecarbonyl system is bonded by way of the 2-position of the pyridine ring are preferred.

Especially preferred are the compounds of formula I or I′

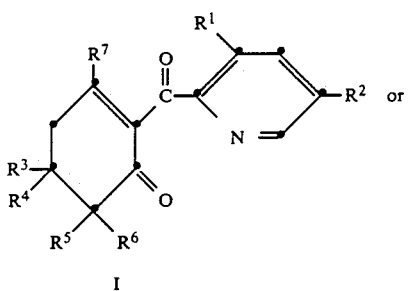

I

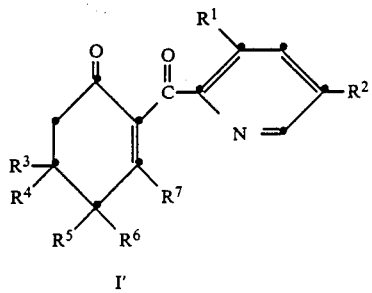

I′ in which $R^1$ is hydrogen; halogen; nitro; cyano; $C_1$-$C_4$alkyl; $C_1$-$C_4$alkoxy; $C_1$-$C_4$alkyl-S(O)$_n$—; COR$^8$; $C_1$-$C_4$haloalkyl; or $C_1$-$C_4$haloalkoxy; $R^2$ is hydrogen; halogen; nitro; cyano; $C_1$-$C_4$alkyl; $C_1$-$C_4$alkoxy; $C_1$-$C_4$haloalkoxy; $C_1$-$C_4$alkyl-S(O)$_n$—; or $C_1$-$C_4$haloalkyl; $R^3$, $R^4$ and $R^5$ independently of one another are each hydrogen; $C_1$-$C_4$alkyl; or phenyl or benzyl each unsubstituted or substituted by up to three identical or different substituents from halogen, nitro, cyano, $C_1$-$C_4$alkyl, $C_1$-$C_4$alkoxy, $C_1$-$C_4$alkyl-S(O)$_n$—, $C_1$-$C_4$haloalkyl, $C_1$-$C_4$haloalkyl-S(O)$_n$— and $C_1$-$C_4$haloalkoxy; $R^6$ is hydrogen; $C_1$-$C_4$alkoxycarbonyl; or cyano; $R^7$ is OH; or O$^\ominus$M$^\oplus$; R8 is OH; $C_1$-$C_4$alkoxy; NH$_2$; $C_1$-$C_4$alkylamino; or di-$C_1$-$C_4$alkylamino; n is 0, 1 or 2; M$^\oplus$ is a cation equivalent of an alkali metal ion, an alkaline earth metal ion or an ammonium ion; of a mono-$C_1$-$C_4$-alkylammonium ion; of a di-$C_1$-$C_4$alkylammonium ion; of a tri-$C_1$-$C_4$alkylammonium ion; or of a triethanolammonium ion.

Of the afore-mentioned compounds of formula I or I′ within the scope of the broadest generic meaning, and also of the emphasised, preferred and especially preferred generic definitions, attention is drawn in each case especially to the sub-groups mentioned below:

(a) Compounds of formula I or I′ in which at least one of the radicals $R^3$ to $R^6$ is hydrogen, (b) Compounds of formula I or I′ in which at least two of the radicals $R^3$ to $R^6$ are hydrogen, (c) Compounds of formula I or I′ in which $R^6$ is cyano and $R^5$ is hydrogen, (d) Compounds of formula I or I′ in which $R^6$ is cyano, $R^5$ is hydrogen and $R^3$ and $R^4$ independently of one another are each hydrogen or $C_1$-$C_{14}$ alkyl, (e) Compounds of formula I or I′ in which $R^6$ is $C_1$-$C_4$alkoxycarbonyl, (f) Compounds of formula I or I′ in which $R^7$ is OH, (g) Compounds of formula I or I′ in which $R^7$ is O$^\ominus$—M$^\oplus$, (h) Compounds of formula I or I′ in which $R^1$ is hydrogen, chlorine, fluorine, nitro, trifluoromethyl, methoxy, bromine, methylthio, methylsulfonyl, carboxy, trichloromethyl or methyl, (i) Compounds of formula I or I′ in which $R^2$ is hydrogen, chlorine, nitro, methylthio, methylsulfinyl, methylsulfonyl, methyl, fluorine, trifluoromethyl or trichloromethyl.

Attention is drawn especially to combinations of the sub-groups (a) to (e) with (h) and (i) both in the form of the free acid (group f)) and in the form of salts (group g)).

Especially preferred are compounds of formula I or I′ in which $R^1$ is hydrogen; fluorine; chlorine; bromine; nitro; cyano; methyl; trifluoromethyl; trichloromethyl; methoxy; methylthio; methylsulfinyl; methylsulfonyl;

carboxy; carbamoyl; methoxycarbonyl; or ethoxycarbonyl; $R^2$ is hydrogen; fluorine; chlorine; nitro; trifluoromethyl; trichloromethyl; methylthio; methylsulfinyl; or methylsulfonyl; $R^3$ is hydrogen; $C_1$–$C_3$alkyl; phenyl; benzyl; or chlorophenyl; $R^4$ is hydrogen; or methyl; $R^5$ is hydrogen; or methyl; $R^6$ is hydrogen; cyano; methyl; or $C_1$–$C_2$alkoxycarbonyl; $R^7$ is OH; or $O^\ominus M^\oplus$; is a cation equivalent of a sodium, lithium, calcium, trimethylammonium or triethanolammonium ion.

The following may be mentioned as individual compounds: 2-(3-chloro-5-trifluoromethylpyridin-2-ylcarbonyl)-cyclohex-1-en-1-ol-3-one and 2-(3-chloro-5-methylsulfonylpyridin-2-ylcarbonyl)-cyclohex-1-en-1-ol-3-one.

The compounds of formula Ia or Ia' in which the radicals $R^1$ to $R^6$ are as defined hereinbefore and $R^7$ is OH can be prepared by (a) reacting a cyclohexanedione of formula II, in which the radicals $R^3$ to $R^6$ are as defined hereinbefore, with a pyridine of formula III, in which $R^1$ and $R^2$ are as defined hereinbefore and X is halogen, preferably chlorine or bromine or the radical

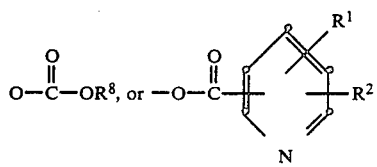

and $R^8$ is $C_1$–$C_4$alkyl, phenyl or benzyl, in the presence of a base

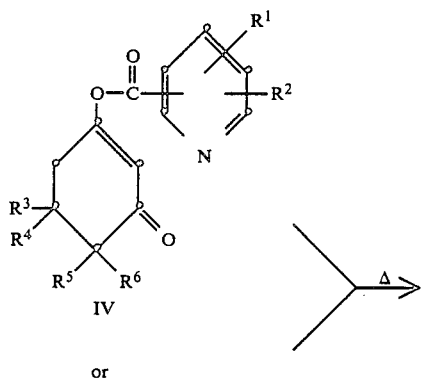

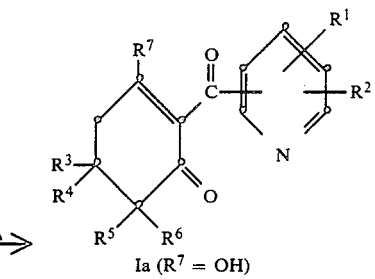

(b) thermal rearrangement of an ester of formula IV or IV' in which the radicals $R^1$ to $R^6$ are as defined hereinbefore

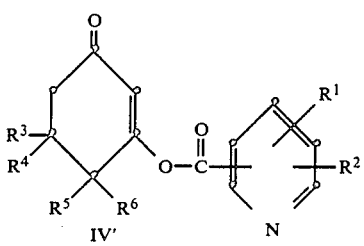

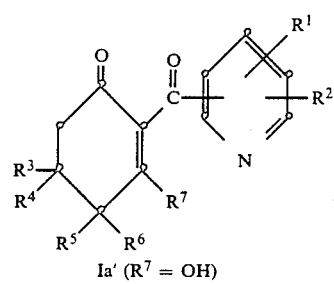

preferably in the presence of cyanide.

The salts of formula Ib and Ib' in which the radicals $R^1$ to $R^6$ are as defined hereinbefore and $R^7$ is $O^\ominus M^\oplus$ can be prepared by (c) reacting a cyclohexanedione Ia or Ia' in which $R^1$ to $R^6$ are as defined hereinbefore and $R^7$ is OH with a base V in which B is $OH^\ominus M^\oplus$, $M^\oplus$ being as defined hereinbefore be oxidised is $C_1$-$C_4$alkyl-S(O)$_n$—with n representing 0, and the remaining radicals are as defined hereinbefore.

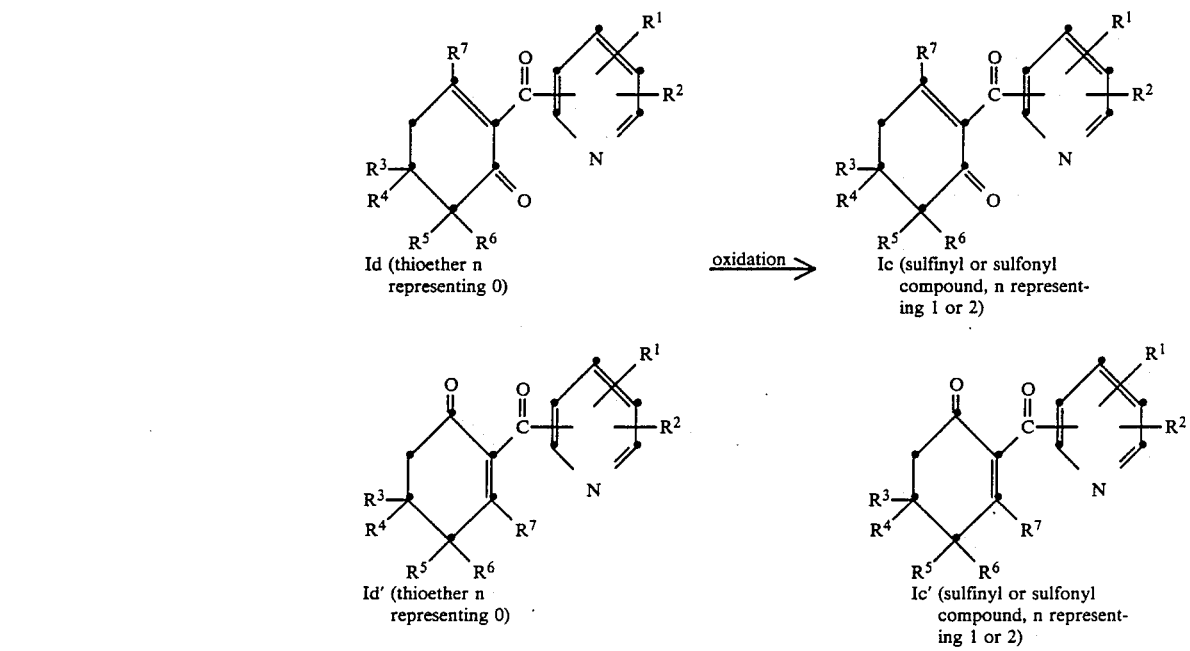

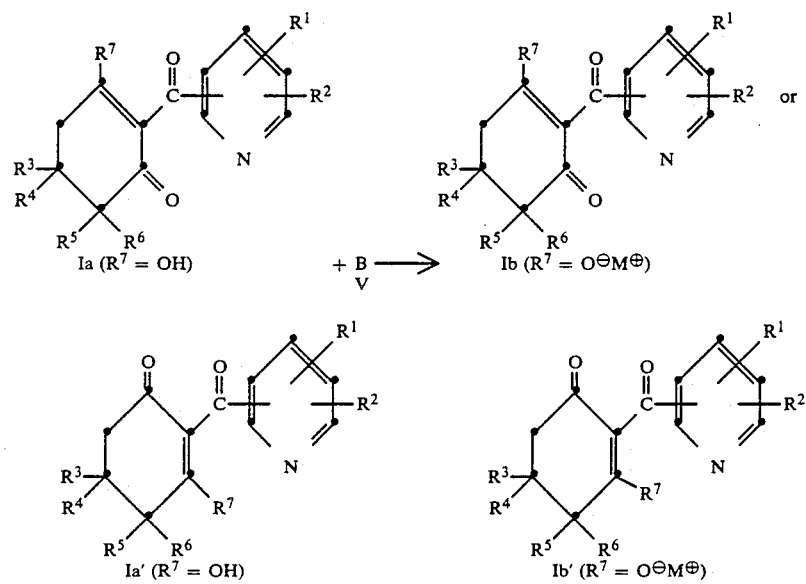

The esters of formula IV and IV' are valuable intermediates for the preparation of the herbicidal end products Ia and Ia' respectively according to process variant (b). The invention thus also relates to the novel esters Iv and IV'. The esters IV and IV' can, however, also be formed as by-products in the acylation according to process variant (a).

(d) Furthermore, the compounds of formula Ic or Ic' in which one or more of the radicals $R^1$ to $R^6$ is (are) $C_1$-$C_4$alkyl-S(O)$_n$—, n representing 1 or 2, and the remaining radicals are as defined hereinbefore, can be prepared by oxidising a thioether of formula Id or Id', wherein the radical from the group $R^1$ to $R^6$ that is to Such oxidations are familiar to the person skilled in the art (for example Methodicum Chimicum, Ed. F. Korte, 9. Thieme Verlag Stuttgart 1976, vol. 7, pages 696-698 and the literature sources mentioned there for oxidation to sulfenes, and vol. 7, pages 751-755 and the literature mentioned there for oxidation to sulfones).

Oxidation with $H_2O_2$ and with per acids, especially with 3-chloroperbenzoic acid, is preferred.

By appropriate selection of bases, solvents and other reaction parameters, such as temperature, concentration etc., the O-acylation may become the main reaction in accordance with the following scheme:

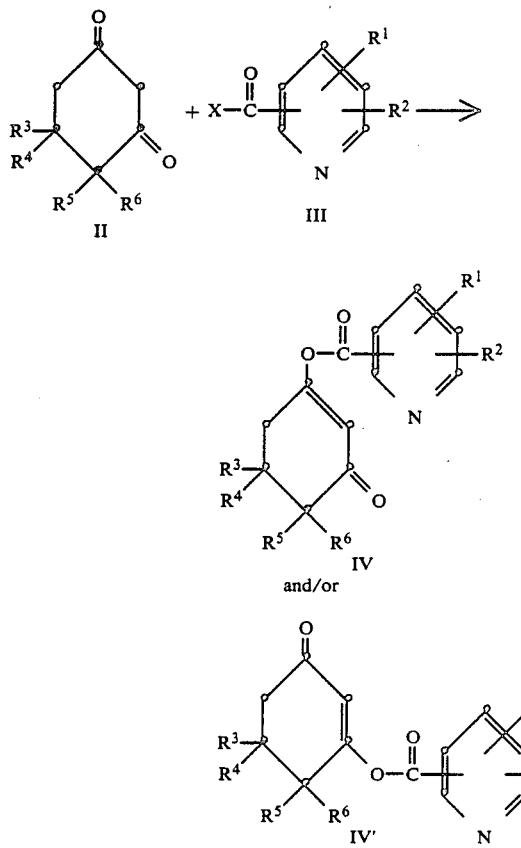

In the C-acylation according to process variant (a) it has proved advantageous to carry out the reaction in the presence of small amounts of cyanide. A low cyanide concentration can be ensured, for example, by the addition of acetone cyanohydrin.

The rearrangement of the esters IV and IV' can also advantageously be carried out under the action of cyanide ions and in the presence of a base.

Although the synthesis of the compounds of formula Ia and Ia' outlined as reaction (a) describes a process by which in principle all compounds included within the scope of formula Ia and Ia' can be produced, for reasons concerning economy and industrial scale production it may be appropriate to convert certain compounds of formula Ia and Ia' into other derivatives included within the scope of formula I and I'. Examples of such conversions, apart from reaction (c) and (d), are, for example, processes in which $R^6$ represents an ester, halogen or cyano radical. These radicals can be converted analogously to the reactions illustrated hereinafter in Scheme 1 (IIa→IIb, IIc or IId) also even at the stage of compounds of formula I. Such derivatisation reactions are familiar to the person skilled in the art.

The above reactions are advantageously carried out in a solvent that is inert with respect to the reactions. Suitable inert solvents are hydrocarbons, such as benzene, toluene or xylene; ethers, such as diethyl ether, methyl isopropyl ether, glyme, diglyme; cyclic ethers, such as tetrahydrofuran and dioxane; ketones, such as acetone, methyl ethyl ketone; amides, such as dimethylformamide, N-methylpyrrolidone; sulfoxides, such as dimethyl sulfoxide; or chlorinated hydrocarbons, such as dichloromethane, trichloromethane, tetrachloromethane or tetrachloroethane, alcohols, such as methanol, ethanol, isopropanol, propanol, butanol etc..

In some cases it is also advantageous to use mixtures of solvents in the form of organic solvents in admixture with water.

The reaction temperature can be varied within wide limits. Suitable reaction temperatures range, for example, from −20° C. to the reflux temperature of the reaction mixture. The reaction is preferably carried out at a temperature of from 0° C. to 100° C.

In the case of reactions (a) and (b) a base is advantageously added. Suitable bases are, inter alia, sodium, potassium and calcium hydroxide, alkali metal and alkaline earth metal carbonates, amines, such as, for example triethylamine, or heterocycles, such as pyridine, 4-dimethylaminopyridine, DABCO and also alkali metal hydrides.

Reactions (a) and (b) can also advantageously be carried out under phase transfer conditions in two-phase systems. Such reactions are familiar to the person skilled in the art (for example described in Dehmlow and Dehmlow, Phase Transfer Catalysis, Verlag Chemie, Weinheim 1983; W. E. Keller, Phase Transfer Reactions Vol. 1 and Vol. 2, G. Thieme Verlag, Stuttgart 1986, 1987).

The cyclohexanediones of formula II are either known or can be prepared analogously to processes known in the literature.

The following malonic ester synthesis is a general method of obtaining the cyclohexanediones II in which first of all, in accordance with the scheme below, the specifically substituted cyclohexanediones IIa, IIb or IIc can be produced from an aldehyde or ketone VI and acetone:

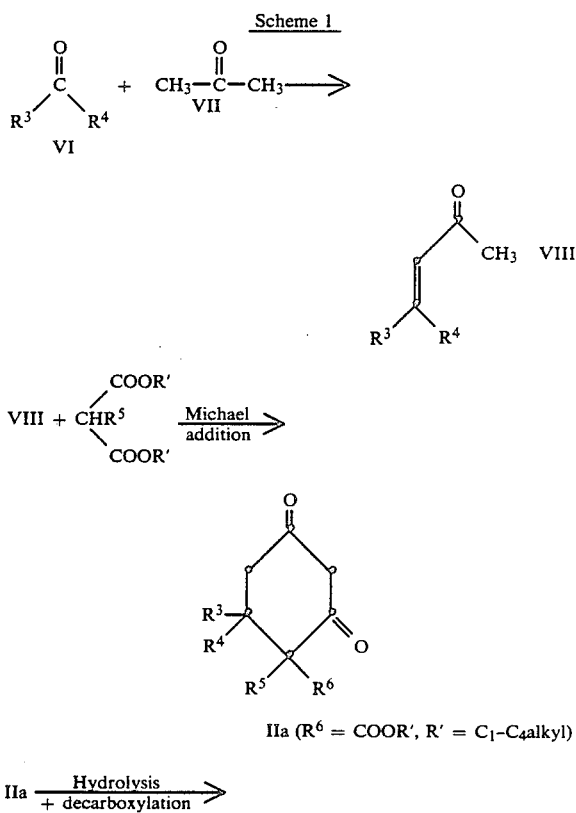

-continued
Scheme 1

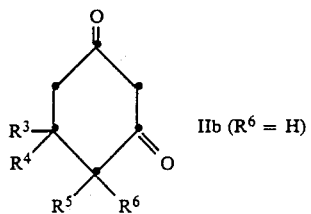

IIb ($R^6$ = H)

The compounds of formula IIc in which the radicals $R^3$ to $R^5$ are as defined hereinbefore and $R^6$ is cyano can be prepared in a modification of reaction scheme 1 by Michael addition of cyanoacetic acid ester XIII, in which $R^5$ is as defined hereinbefore and R' is $C_1$-$C_4$alkyl, to the ketone VIII, in which $R^3$ and $R^4$ are as defined hereinbefore.

Scheme 2

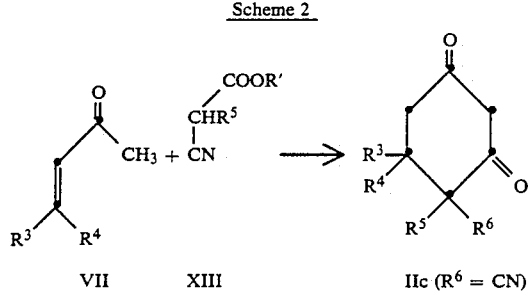

VII            XIII           IIc ($R^6$ = CN)

Of the pyridinecarboxylic acid derivatives III, it is especially the acid chlorides that are preferred.

The pyridine-2-carboxylic acid chloride IIIa may advantageously be prepared by a Pd-catalysed carbonylation reaction in accordance with the following reaction scheme 3:

Scheme 3

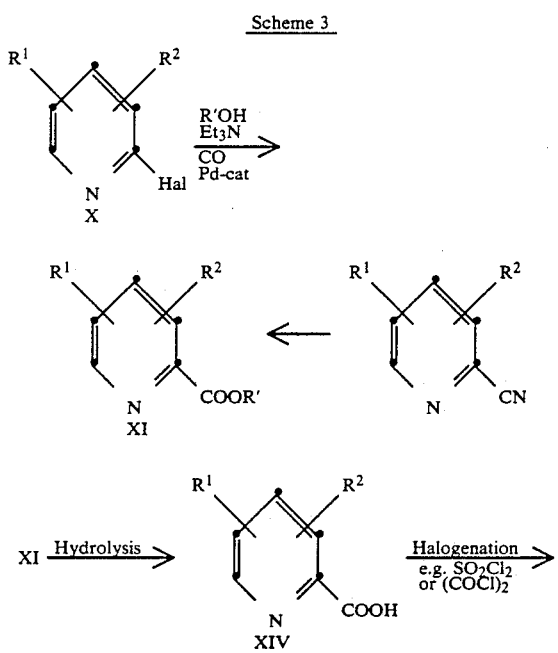

-continued
Scheme 3

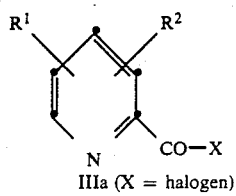

IIIa (X = halogen)

In the above scheme, Hal is halogen (especially chlorine); R' is $C_1$-$C_4$alkyl and Pd-Cat is preferably $PdCl_2(TPP)_2$ a triphenylphosphine complex of palladium.

The picolinic acid derivatives XI, IIIa and XIV mentioned in scheme 3 are valuable intermediates for the synthesis of the cyclohexanediones I of the invention. Most of these compounds are novel.

The invention thus also relates to the novel picolinic acid derivatives of formula XV

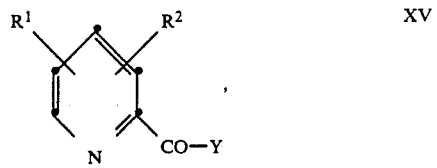

in which Y is OH; $C_1$-$C_4$alkoxy; or halogen; and $R^1$ and $R^2$ independently of one another are each halogen; nitro; cyano; $C_1$-$C_4$haloalkyl; $C_1$-$C_4$alkyl; $C_1$-$C_4$alkoxy; or $C_1$-$C_4$alkyl-S(O)$_n$—; n is 0; 1; or 2; with the proviso that when Y is chlorine and the radical $R^1$ is bonded in position 3 and the radical $R^2$ is bonded in position 5, $R^1$ and $R^2$ are not simultaneously chlorine or simultaneously methyl, or when $R^1$ is nitro $R^2$ is not methyl.

Preferred are picolinic acid derivatives of formula XV'

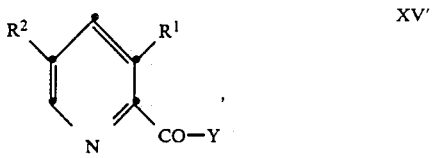

in which Y is OH; $C_1$-$C_4$alkoxy; or halogen; and $R^1$ and $R^2$ independently of one another are each halogen; nitro; cyano; $C_1$-$C_4$haloalkyl; $C_1$-$C_4$alkyl; $C_1$-$C_4$alkoxy; or $C_1$-$C_4$alkyl-S(O)$_n$—; and n is 0; 1; or 2; with the proviso that when Y is chlorine, $R^1$ and $R^2$ are not simultaneously chlorine or simultaneously methyl, or $R^1$ nitro and R methyl.

Especially preferred are the compounds of formula XV' in which Y is OH; $C_1$-$C_4$alkoxy; or halogen; $R^1$ is hydrogen; and $R^2$ is $C_1$-$C_4$alkoxy, $C_1$-$C_4$haloalkyl; or cyano.

Also especially preferred are compounds of formula XV' in which Y is OH; $C_1$-$C_4$alkoxy; or halogen; $R^1$ is $C_1$-$C_4$alkoxy; $C_1$-$C_4$haloalkyl; or cyano; and $R^2$ is hydrogen.

Of the compounds of formula XV, and the compounds XV' mentioned as preferred and especially preferred, attention is drawn to the acid chlorides, that is to say those compounds in which Y is chlorine.

The compounds of formula I are highly active ingredients for plants that at suitable rates of application are excellently suitable as selective herbicides for controlling weeds in crops of useful plants. That is to say, at such rates of application the active ingredients of formula I are distinguished by a good selective herbicidal property against weeds. In particular, cereals, such as rye, barley, oats, wheat and maize, but also other crop plants, such as sorghum, rice, cotton, sugar cane or soybeans or also permanent crops (such as, for example, vines or plantations) remain virtually undamaged at low rates of application. At increased rates of application the growth of the crop plants is influenced only to a small extent. If the rates of application are very high, the substances of formula I have total herbicidal properties. The rates of application are generally from 0.001 to 4 kg. preferably from 0.005 to 2 kg of active substance per hectare.

At high rates of application the compounds of formula I can also be used as total herbicides. They are especially suitable for controlling weeds on paths, in public areas, on railway tracks or in other areas in which a total kill of the plants growing there is desired.

The selective herbicidal activity of the compounds of the invention is observed both in pre-emergence and post-emergence application. These compounds can therefore be used with equal success pre- or post-emergence in selective weed control.

Advantageously, the compounds or compositions of the invention can be applied also to the propagation material of the crop plant. Seed dressing, especially, may be mentioned here. Propagation material is seeds, plantlets or other parts of the plant from which the crop plants can be reared. The invention also relates to the propagation material treated with an effective amount of a compound of formula I.

The invention relates also to herbicidal compositions that contain a novel compound of formula I, and to methods for pre-and post-emergence weed control.

The compounds of formula I are used in unmodified form or, preferably, in the form of compositions together with the adjuvants conventionally employed in the art of formulation, and are therefore formulated in known manner e.g. into emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant or extender, are prepared in known manner, e.g. by homogeneously mixing and/or grinding the active ingredients with extenders, e.g. solvents, solid carriers and, where appropriate, surface-active compounds (surfactants).

Suitable solvents or extenders are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids.

These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_4$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

Surfactants customary in the art of formulation are described, inter alia, in the following publications: "1986 International Mc Cutcheon's Emulsifiers and Detergents", Glen Rock, N.J., USA, 1986; H. Stache "Tensid Taschenbuch", 2nd edition, C. Hanser Verlag, Munich/Vienna, 1981; M. and J. Ash. "Encyclopedia of Surfactants", Vol. I–III, Chemical Publishing Co., New York, 1980–1981.

The active ingredient preparations usually contain 0.1 to 95%, preferably 0.1 to 80%, of a compound of formula I, 1 to 99.9% of one or more solid or liquid adjuvants, and 0 to 25% of a surfactant.

Preferred formulations are composed especially as follows (throughout, percentages are by weight)

| Emulsifiable concentrates | |
| --- | --- |
| active ingredient | 1 to 20%, preferably 5 to 10% |
| surfactant | 5 to 30%, preferably 10 to 20% |
| liquid carrier | 50 to 94%, preferably 70 to 85%. |
| Dusts | |
| active ingredient | 0.1 to 10%, preferably 0.1 to 1% |
| solid carrier | 99.9 to 90%, preferably 99.9 to 99%. |
| Suspension concentrates | |
| active ingredient | 5 to 75%, preferably 10 to 50% |
| water | 94 to 25%, preferably 88 to 30% |
| surfactant | 1 to 40%, preferably 2 to 30%. |
| Wettable powders | |
| active ingredient | 0.5 to 90%, preferably 1 to 80% |
| surfactant | 0.5 to 20%, preferably 1 to 15% |
| solid carrier | 5 to 95%, preferably 15 to 90%. |
| Granulates | |
| active ingredient | 0.5 to 30%, preferably 3 to 15% |
| solid carrier | 99.5 to 70%, preferably 97 to 85%. |

Whereas commercial products will preferably be formulated as concentrates, the end user will normally employ dilute formulations. The formulations can be diluted to a concentration as low as 0.001% active ingredient.

The compositions may also contain further additives such as stabilisers, antifoams, viscosity regulators, binders, tackifiers and also fertilisers or other active ingredients for obtaining special effects.

The following Examples illustrate the invention.

P. PREPARATION EXAMPLES

P.1. Compounds of formula I

P.1.1. Reactions with cyclohexanediones of formula II

P.1.1.1. 2-(3-chloro-5-trifluoromethylpyridin-2-ylcarbonyl)-cyclohex1-en-1-ol-3-one 4.9 g (20 mmol) of 3-chloro-5-trifluoromethylpyridine-2-carboxylic acid chloride are added dropwise to a solution of 2.2 g (20 mmol) of 1,3-cyclohexanedione and 7 ml (50 mmol) of triethylamine in 25 ml of dichloromethane, the temperature rising to 35° C. The whole is then stirred at room temperature for 15 hours to complete the reaction. The black suspension is diluted with 250 ml of dichloromethane, adjusted to pH 1 with 1N HCl at from 0° to 5°, and washed twice with $H_2O$. The product is subsequently extracted with 5% $NaHCO_3$ solution, precipitated cold with 37% HCl, filtered with suction and dried. 4.0 g (63%) of the title compound of formula

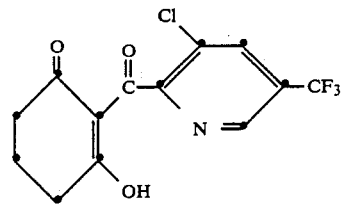

are isolated in the form of crystals having a melting point of 102°–105° C. (Compound No. 1.005).

P.1.1.2. 2-(5-trifluoromethylpyrid-2-ylcarbonl)-cyclohex-1-en-1-ol-3-one 20.4 g (85 mmol) of 5-trifluoromethylpyridine-2-carboxylic acid chloride are added dropwise at from 20° to 25° C. to a solution of 9.5 g (85 mmol) of 1,3-cyclohexanedione and 24 ml (170 mmol) of triethylamine in 85 ml of dichloromethane. After the whole has been stirred for 4 hours at room temperature, 0.8 ml of acetone cyanohydrin is added and stirring is continued for a further 15 hours. The reaction solution is diluted with 200 ml of dichloromethane, adjusted to pH 1 with 1N HCl at from 0° to 5° C., washed twice with water and extracted with 5% $NaHCO_3$ solution. The extract is washed with dichloromethane, adjusted to pH 1 with 37% HCl, and the precipitated product is filtered with suction and dried.

17.2 g (71%) of the title compound of formula

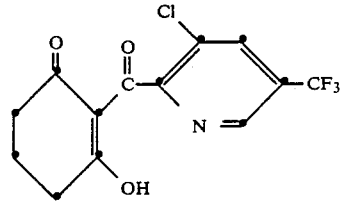

are isolated in the form of crystals having a melting point of 95°–97° C. (Compound No. 1.010).

The compounds of Table 1 can be synthesised analogously to the aforedescribed preparation process.

P.1.1.3. 2-(3-chloro-5-methylthiopyridin-2-ylcarbonyl)-cyclohex-1-en-1-ol-3-one 4.4 g (0.048 mol) of 1,3-cyclohexanedione and 10.6 g (0.048 mol) of 3-chloro-5-methylthiopyridine-2-carboxylic acid chloride are reacted analogously to P.1.1.1. and purified.

7.2 g (50.4%) of the title compound of formula

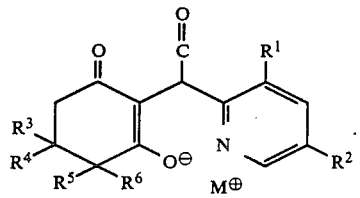

are isolated in the form of crystals having a melting point of 113° C. (decomp.) (Compound No. 1.018).

P.1.1.4. 2-(3-Chloro-5-methylsulfonyl-pyridin-2-yl-carbonyl)-cyclohex-1-en-1-ol-3-one A solution of 5.6 g (50 mmol) 1.3-cyclohexanedione and 14 ml (100 mmol) of triethylamine in 50 ml dichloromethane is added at 0° to 5° C. to a suspension of 10.2 g (40 mmol) 3-chloro-5-methylsulfonyl-pyridine-2-carboxylic acid chloride in 80 ml dichloromethane. After stirring for 3 hours at room temperature 0.5 ml of aceton cyanhydrin are added to the suspension thus obtained. Stirring is continued for 3 hours at room temperature. The dark brown suspension is then diluted with 200 ml dichloromethane, adjusted to pH 1 with 1N HCl, and washed twice with water. The product is subsequently extracted with 5% NaHCO₃ solution, precipitated cold with 37% HCl, filtered with suction and dried.

10.4 g (78.9%) of the title compound of formula

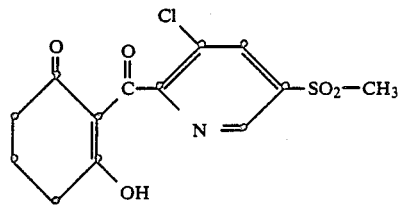

are isolated in the form of white crystals having a melting point of >200° C. (under decomp.) (Compound No. 1.020).

P.1.2.1. Preparation of 2-(3-chloro-5-methylsulfonyl-pyridin-2-yl-carbonyl) -cyclohex-1-en-1-ol-3one A solution of 4.1 g (0.02 mol) of 85% 3-chloroperbenzoic acid in 50 ml of dichloromethane is added dropwise to a solution of 3 g (0.01 mol) of 2-(3-chloro-5-methyl-thiopyridin-2-ylcarbonyl)-cyclohex-1-en-1-ol-3-one in 25 ml of dichloromethane with cooling at from 20° to 30° C. The whole is then stirred at room temperature for 4 hours. The yellow suspension is filtered off from the chlorobenzoic acid and concentrated by evaporation on a rotary evaporator. The resulting mass is triturated with 50 ml of ether, filtered with suction and dried.

1.8 g (51.6%) of the title compound of formula

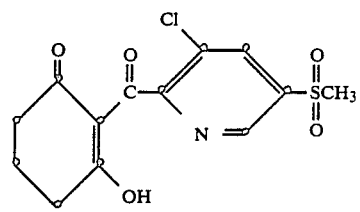

are obtained in the form of crystals having a melting point of 150° C. (decomp.) (Compound No. 1.020).

TABLE 1

Compounds of formula

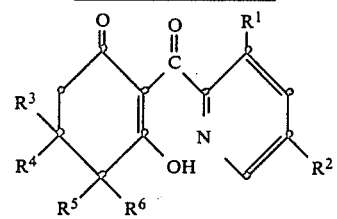

| Comp. No. | R¹ | R² | R³ | R⁴ | R⁵ | R⁶ | phys. data |
|---|---|---|---|---|---|---|---|
| 1.001 | Cl | Cl | H | H | H | H | m.p. 144–146° C. |
| 1.002 | Cl | H | H | H | H | H | |
| 1.003 | H | Cl | H | H | H | H | m.p. 106–107° C. |
| 1.004 | H | H | H | H | H | H | resin |
| 1.005 | Cl | CF₃ | H | H | H | H | m.p. 102–105° C. |
| 1.006 | NO₂ | H | H | H | H | H | |
| 1.007 | H | NO₂ | H | H | H | H | |
| 1.008 | NO₂ | Cl | H | H | H | H | |
| 1.009 | CF₃ | H | H | H | H | H | |
| 1.010 | H | CF₃ | H | H | H | H | m.p. 95–97° C. |
| 1.011 | OCH₃ | H | H | H | H | H | |
| 1.012 | CN | H | H | H | H | H | |
| 1.013 | OCH₃ | Cl | H | H | H | H | |
| 1.014 | CN | Cl | H | H | H | H | |
| 1.015 | Br | Cl | H | H | H | H | |
| 1.016 | SCH₃ | Cl | H | H | H | H | |
| 1.017 | SO₂CH₃ | Cl | H | H | H | H | |
| 1.018 | Cl | SCH₃ | H | H | H | H | m.p. >113° C. (decomp.) |

TABLE 1-continued

Compounds of formula

| Comp. No. | R$^1$ | R$^2$ | R$^3$ | R$^4$ | R$^5$ | R$^6$ | phys. data |
|---|---|---|---|---|---|---|---|
| 1.019 | Cl | SOCH$_3$ | H | H | H | H | m.p. 134–136° C. |
| 1.020 | Cl | SO$_2$CH$_3$ | H | H | H | H | m.p. >150° C. (decomp.) |
| 1.021 | SOCH$_3$ | Cl | H | H | H | H | |
| 1.022 | SO$_2$CH$_3$ | H | H | H | H | H | |
| 1.023 | H | SO$_2$CH$_3$ | H | H | H | H | |
| 1.024 | H | CH$_3$ | H | H | H | H | |
| 1.025 | Cl | F | H | H | H | H | m.p. 113–115° C. |
| 1.026 | H | CF$_3$ | H | H | H | H | |
| 1.027 | F | F | H | H | H | H | |
| 1.028 | F | CF$_3$ | H | H | H | H | |
| 1.029 | CF$_3$ | F | H | H | H | H | |
| 1.030 | H | CCl$_3$ | H | H | H | H | |
| 1.031 | CCl$_3$ | H | H | H | H | H | |
| 1.032 | Cl | CCl$_3$ | H | H | H | H | |
| 1.033 | CCl$_3$ | Cl | H | H | H | H | |
| 1.034 | CH$_3$ | H | H | H | H | H | |
| 1.035 | Cl | Cl | CH$_3$ | H | H | H | m.p. 117–124° C. |
| 1.036 | Cl | H | CH$_3$ | H | H | H | |
| 1.037 | H | Cl | CH$_3$ | H | H | H | |
| 1.038 | H | H | CH$_3$ | H | H | H | |
| 1.039 | Cl | CF$_3$ | CH$_3$ | H | H | H | Fp. 93–103° C. |
| 1.040 | NO$_2$ | H | CH$_3$ | H | H | H | |
| 1.041 | H | NO$_2$ | CH$_3$ | H | H | H | |
| 1.042 | NO$_2$ | Cl | CH$_3$ | H | H | H | |
| 1.043 | CF$_3$ | H | CH$_3$ | H | H | H | |
| 1.044 | H | CF$_3$ | CH$_3$ | H | H | H | m.p. 99–101° C. |
| 1.045 | OCH$_3$ | H | CH$_3$ | H | H | H | |
| 1.046 | CN | H | CH$_3$ | H | H | H | |
| 1.047 | OCH$_3$ | Cl | CH$_3$ | H | H | H | |
| 1.048 | CN | Cl | CH$_3$ | H | H | H | |
| 1.049 | Br | Cl | CH$_3$ | H | H | H | |
| 1.050 | SCH$_3$ | Cl | CH$_3$ | H | H | H | |
| 1.051 | SO$_2$CH$_3$ | Cl | CH$_3$ | H | H | H | |
| 1.052 | Cl | SCH$_3$ | CH$_3$ | H | H | H | |
| 1.053 | Cl | SOCH$_3$ | CH$_3$ | H | H | H | |
| 1.054 | Cl | SO$_2$CH$_3$ | CH$_3$ | H | H | H | |
| 1.055 | SOCH$_3$ | Cl | CH$_3$ | H | H | H | |
| 1.056 | SO$_2$CH$_3$ | H | CH$_3$ | H | H | H | |
| 1.057 | H | SO$_2$CH$_3$ | CH$_3$ | H | H | H | |
| 1.058 | H | CH$_3$ | CH$_3$ | H | H | H | |
| 1.059 | Cl | F | CH$_3$ | H | H | H | |
| 1.060 | H | CF$_3$ | CH$_3$ | H | H | H | |
| 1.061 | F | F | CH$_3$ | H | H | H | |
| 1.062 | F | CF$_3$ | CH$_3$ | H | H | H | |
| 1.063 | CF$_3$ | F | CH$_3$ | H | H | H | |
| 1.064 | H | CCl$_3$ | CH$_3$ | H | H | H | |
| 1.065 | CCl$_3$ | H | CH$_3$ | H | H | H | |
| 1.066 | Cl | CCl$_3$ | CH$_3$ | H | H | H | |
| 1.067 | CCl$_3$ | Cl | CH$_3$ | H | H | H | |
| 1.068 | CH$_3$ | H | CH$_3$ | H | H | H | |
| 1.069 | Cl | Cl | C$_2$H$_5$ | H | H | H | |
| 1.070 | Cl | H | C$_2$H$_5$ | H | H | H | |
| 1.071 | H | Cl | C$_2$H$_5$ | H | H | H | |
| 1.072 | H | H | C$_2$H$_5$ | H | H | H | |
| 1.073 | Cl | CF$_3$ | C$_2$H$_5$ | H | H | H | |
| 1.074 | NO$_2$ | H | C$_2$H$_5$ | H | H | H | |
| 1.075 | H | NO$_2$ | C$_2$H$_5$ | H | H | H | |
| 1.076 | NO$_2$ | Cl | C$_2$H$_5$ | H | H | H | |
| 1.077 | CF$_3$ | H | C$_2$H$_5$ | H | H | H | |
| 1.078 | H | CF$_3$ | C$_2$H$_5$ | H | H | H | |
| 1.079 | OCH$_3$ | H | C$_2$H$_5$ | H | H | H | |
| 1.080 | CN | H | C$_2$H$_5$ | H | H | H | |
| 1.081 | OCH$_3$ | Cl | C$_2$H$_5$ | H | H | H | |
| 1.082 | CN | Cl | C$_2$H$_5$ | H | H | H | |
| 1.083 | Br | Cl | C$_2$H$_5$ | H | H | H | |
| 1.084 | SCH$_3$ | Cl | C$_2$H$_5$ | H | H | H | |
| 1.085 | SO$_2$CH$_3$ | Cl | C$_2$H$_5$ | H | H | H | |

TABLE 1-continued

Compounds of formula

| Comp. No. | R¹ | R² | R³ | R⁴ | R⁵ | R⁶ | phys. data |
|---|---|---|---|---|---|---|---|
| 1.086 | Cl | SCH$_3$ | C$_2$H$_5$ | H | H | H | |
| 1.087 | Cl | SOCH$_3$ | C$_2$H$_5$ | H | H | H | |
| 1.088 | Cl | SO$_2$CH$_3$ | C$_2$H$_5$ | H | H | H | |
| 1.089 | SOCH$_3$ | Cl | C$_2$H$_5$ | H | H | H | |
| 1.090 | SO$_2$CH$_3$ | H | C$_2$H$_5$ | H | H | H | |
| 1.091 | H | SO$_2$CH$_3$ | C$_2$H$_5$ | H | H | H | |
| 1.092 | H | CH$_3$ | C$_2$H$_5$ | H | H | H | |
| 1.093 | Cl | F | C$_2$H$_5$ | H | H | H | |
| 1.094 | H | CF$_3$ | C$_2$H$_5$ | H | H | H | |
| 1.095 | F | F | C$_2$H$_5$ | H | H | H | |
| 1.096 | F | CF$_3$ | C$_2$H$_5$ | H | H | H | |
| 1.097 | CF$_3$ | F | C$_2$H$_5$ | H | H | H | |
| 1.098 | H | CCl$_3$ | C$_2$H$_5$ | H | H | H | |
| 1.099 | CCl$_3$ | H | C$_2$H$_5$ | H | H | H | |
| 1.100 | Cl | CCl$_3$ | C$_2$H$_5$ | H | H | H | |
| 1.101 | CCl$_3$ | Cl | C$_2$H$_5$ | H | H | H | |
| 1.102 | CH$_3$ | H | C$_2$H$_5$ | H | H | H | |
| 1.103 | Cl | Cl | n-C$_3$H$_7$ | H | H | H | |
| 1.104 | Cl | H | n-C$_3$H$_7$ | H | H | H | |
| 1.105 | H | Cl | n-C$_3$H$_7$ | H | H | H | |
| 1.106 | H | H | n-C$_3$H$_7$ | H | H | H | |
| 1.107 | Cl | CF$_3$ | n-C$_3$H$_7$ | H | H | H | |
| 1.108 | NO$_2$ | H | n-C$_3$H$_7$ | H | H | H | |
| 1.109 | H | NO$_2$ | n-C$_3$H$_7$ | H | H | H | |
| 1.110 | NO$_2$ | Cl | n-C$_3$H$_7$ | H | H | H | |
| 1.111 | CF$_3$ | H | n-C$_3$H$_7$ | H | H | H | |
| 1.112 | H | CF$_3$ | n-C$_3$H$_7$ | H | H | H | |
| 1.113 | OCH$_3$ | H | n-C$_3$H$_7$ | H | H | H | |
| 1.114 | CN | H | n-C$_3$H$_7$ | H | H | H | |
| 1.115 | OCH$_3$ | Cl | n-C$_3$H$_7$ | H | H | H | |
| 1.116 | CN | Cl | n-C$_3$H$_7$ | H | H | H | |
| 1.117 | Br | Cl | n-C$_3$H$_7$ | H | H | H | |
| 1.118 | SCH$_3$ | Cl | n-C$_3$H$_7$ | H | H | H | |
| 1.119 | SO$_2$CH$_3$ | Cl | n-C$_3$H$_7$ | H | H | H | |
| 1.120 | Cl | SCH$_3$ | n-C$_3$H$_7$ | H | H | H | |
| 1.121 | Cl | SOCH$_3$ | n-C$_3$H$_7$ | H | H | H | |
| 1.122 | Cl | SO$_2$CH$_3$ | n-C$_3$H$_7$ | H | H | H | |
| 1.123 | SOCH$_3$ | Cl | n-C$_3$H$_7$ | H | H | H | |
| 1.124 | SO$_2$CH$_3$ | H | n-C$_3$H$_7$ | H | H | H | |
| 1.125 | H | SO$_2$CH$_3$ | n-C$_3$H$_7$ | H | H | H | |
| 1.126 | H | CH$_3$ | n-C$_3$H$_7$ | H | H | H | |
| 1.127 | Cl | F | n-C$_3$H$_7$ | H | H | H | |
| 1.128 | H | CF$_3$ | n-C$_3$H$_7$ | H | H | H | |
| 1.129 | F | F | n-C$_3$H$_7$ | H | H | H | |
| 1.130 | F | CF$_3$ | n-C$_3$H$_7$ | H | H | H | |
| 1.131 | CF$_3$ | F | n-C$_3$H$_7$ | H | H | H | |
| 1.132 | H | CCl$_3$ | n-C$_3$H$_7$ | H | H | H | |
| 1.133 | CCl$_3$ | H | n-C$_3$H$_7$ | H | H | H | |
| 1.134 | Cl | CCl$_3$ | n-C$_3$H$_7$ | H | H | H | |
| 1.135 | CCl$_3$ | Cl | n-C$_3$H$_7$ | H | H | H | |
| 1.136 | CH$_3$ | H | n-C$_3$H$_7$ | H | H | H | |
| 1.137 | Cl | Cl | i-C$_3$H$_7$ | H | H | H | |
| 1.138 | Cl | H | i-C$_3$H$_7$ | H | H | H | |
| 1.139 | H | Cl | i-C$_3$H$_7$ | H | H | H | |
| 1.140 | H | H | i-C$_3$H$_7$ | H | H | H | |
| 1.141 | Cl | CF$_3$ | i-C$_3$H$_7$ | H | H | H | m.p. 72–75° C. |
| 1.142 | NO$_2$ | H | i-C$_3$H$_7$ | H | H | H | |
| 1.143 | H | NO$_2$ | i-C$_3$H$_7$ | H | H | H | |
| 1.144 | NO$_2$ | Cl | i-C$_3$H$_7$ | H | H | H | |
| 1.145 | CF$_3$ | H | i-C$_3$H$_7$ | H | H | H | |
| 1.146 | H | CF$_3$ | i-C$_3$H$_7$ | H | H | H | m.p. 103–106° C. |
| 1.147 | OCH$_3$ | H | i-C$_3$H$_7$ | H | H | H | |
| 1.148 | CN | H | i-C$_3$H$_7$ | H | H | H | |
| 1.149 | OCH$_3$ | Cl | i-C$_3$H$_7$ | H | H | H | |
| 1.150 | CN | Cl | i-C$_3$H$_7$ | H | H | H | |
| 1.151 | Br | Cl | i-C$_3$H$_7$ | H | H | H | |
| 1.152 | SCH$_3$ | Cl | i-C$_3$H$_7$ | H | H | H | |
| 1.153 | SO$_2$CH$_3$ | Cl | i-C$_3$H$_7$ | H | H | H | |

TABLE 1-continued

Compounds of formula

| Comp. No. | R¹ | R² | R³ | R⁴ | R⁵ | R⁶ | phys. data |
|---|---|---|---|---|---|---|---|
| 1.154 | Cl | SCH₃ | i-C₃H₇ | H | H | H | |
| 1.155 | Cl | SOCH₃ | i-C₃H₇ | H | H | H | |
| 1.156 | Cl | SO₂CH₃ | i-C₃H₇ | H | H | H | |
| 1.157 | SOCH₃ | Cl | i-C₃H₇ | H | H | H | |
| 1.158 | SO₂CH₃ | H | i-C₃H₇ | H | H | H | |
| 1.159 | H | SO₂CH₃ | i-C₃H₇ | H | H | H | |
| 1.160 | H | CH₃ | i-C₃H₇ | H | H | H | |
| 1.161 | Cl | F | i-C₃H₇ | H | H | H | |
| 1.162 | H | CF₃ | i-C₃H₇ | H | H | H | |
| 1.163 | F | F | i-C₃H₇ | H | H | H | |
| 1.164 | F | CF₃ | i-C₃H₇ | H | H | H | |
| 1.165 | CF₃ | F | i-C₃H₇ | H | H | H | |
| 1.166 | H | CCl₃ | i-C₃H₇ | H | H | H | |
| 1.167 | CCl₃ | H | i-C₃H₇ | H | H | H | |
| 1.168 | Cl | CCl₃ | i-C₃H₇ | H | H | H | |
| 1.169 | CCl₃ | Cl | i-C₃H₇ | H | H | H | |
| 1.170 | CH₃ | H | i-C₃H₇ | H | H | H | |
| 1.171 | Cl | Cl | n-C₃H₇ | H | H | COOC₂H₅ | |
| 1.172 | Cl | H | n-C₃H₇ | H | H | COOC₂H₅ | |
| 1.173 | H | Cl | n-C₃H₇ | H | H | COOC₂H₅ | |
| 1.174 | H | H | n-C₃H₇ | H | H | COOC₂H₅ | |
| 1.175 | Cl | CF₃ | n-C₃H₇ | H | H | COOC₂H₅ | |
| 1.176 | NO₂ | H | n-C₃H₇ | H | H | COOC₂H₅ | |
| 1.177 | H | NO₂ | n-C₃H₇ | H | H | COOC₂H₅ | |
| 1.178 | NO₂ | Cl | n-C₃H₇ | H | H | COOC₂H₅ | |
| 1.179 | CF₃ | H | n-C₃H₇ | H | H | COOC₂H₅ | |
| 1.180 | H | CF₃ | n-C₃H₇ | H | H | COOC₂H₅ | |
| 1.181 | OCH₃ | H | n-C₃H₇ | H | H | COOC₂H₅ | |
| 1.182 | CN | H | n-C₃H₇ | H | H | COOC₂H₅ | |
| 1.183 | OCH₃ | Cl | n-C₃H₇ | H | H | COOC₂H₅ | |
| 1.184 | CN | Cl | n-C₃H₇ | H | H | COOC₂H₅ | |
| 1.185 | Br | Cl | n-C₃H₇ | H | H | COOC₂H₅ | |
| 1.186 | SCH₃ | Cl | n-C₃H₇ | H | H | COOC₂H₅ | |
| 1.187 | SO₂CH₃ | Cl | n-C₃H₇ | H | H | COOC₂H₅ | |
| 1.188 | Cl | SCH₃ | n-C₃H₇ | H | H | COOC₂H₅ | |
| 1.189 | Cl | SOCH₃ | n-C₃H₇ | H | H | COOC₂H₅ | |
| 1.190 | Cl | SO₂CH₃ | n-C₃H₇ | H | H | COOC₂H₅ | |
| 1.191 | SOCH₃ | Cl | n-C₃H₇ | H | H | COOC₂H₅ | |
| 1.192 | SO₂CH₃ | H | n-C₃H₇ | H | H | COOC₂H₅ | |
| 1.193 | H | SO₂CH₃ | n-C₃H₇ | H | H | COOC₂H₅ | |
| 1.194 | H | CH₃ | n-C₃H₇ | H | H | COOC₂H₅ | |
| 1.195 | Cl | F | n-C₃H₇ | H | H | COOC₂H₅ | |
| 1.196 | H | CF₃ | n-C₃H₇ | H | H | COOC₂H₅ | |
| 1.197 | F | F | n-C₃H₇ | H | H | COOC₂H₅ | |
| 1.198 | F | CF₃ | n-C₃H₇ | H | H | COOC₂H₅ | |
| 1.199 | CF₃ | F | n-C₃H₇ | H | H | COOC₂H₅ | |
| 1.200 | H | CCl₃ | n-C₃H₇ | H | H | COOC₂H₅ | |
| 1.201 | CCl₃ | H | n-C₃H₇ | H | H | COOC₂H₅ | |
| 1.202 | Cl | CCl₃ | n-C₃H₇ | H | H | COOC₂H₅ | |
| 1.203 | CCl₃ | Cl | n-C₃H₇ | H | H | COOC₂H₅ | |
| 1.204 | CH₃ | H | n-C₃H₇ | H | H | COOC₂H₅ | |
| 1.205 | Cl | Cl | i-C₃H₇ | H | H | COOCH₃ | |
| 1.206 | Cl | H | i-C₃H₇ | H | H | COOCH₃ | |
| 1.207 | H | Cl | i-C₃H₇ | H | H | COOCH₃ | |
| 1.208 | H | H | i-C₃H₇ | H | H | COOCH₃ | |
| 1.209 | Cl | CF₃ | i-C₃H₇ | H | H | COOCH₃ | m.p. 91–92° C. |
| 1.210 | NO₂ | H | i-C₃H₇ | H | H | COOCH₃ | |
| 1.211 | H | NO₂ | i-C₃H₇ | H | H | COOCH₃ | |
| 1.212 | NO₂ | Cl | i-C₃H₇ | H | H | COOCH₃ | |
| 1.213 | CF₃ | H | i-C₃H₇ | H | H | COOCH₃ | |
| 1.214 | H | CF₃ | i-C₃H₇ | H | H | COOCH₃ | |
| 1.215 | OCH₃ | H | i-C₃H₇ | H | H | COOCH₃ | |
| 1.216 | CN | H | i-C₃H₇ | H | H | COOCH₃ | |
| 1.217 | OCH₃ | Cl | i-C₃H₇ | H | H | COOCH₃ | |
| 1.218 | CN | Cl | i-C₃H₇ | H | H | COOCH₃ | |
| 1.219 | Br | Cl | i-C₃H₇ | H | H | COOCH₃ | |
| 1.220 | SCH₃ | Cl | i-C₃H₇ | H | H | COOCH₃ | |
| 1.221 | SO₂CH₃ | Cl | i-C₃H₇ | H | H | COOCH₃ | |

TABLE 1-continued

Compounds of formula

| Comp. No. | R¹ | R² | R³ | R⁴ | R⁵ | R⁶ | phys. data |
|---|---|---|---|---|---|---|---|
| 1.222 | Cl | SCH$_3$ | i-C$_3$H$_7$ | H | H | COOCH$_3$ | |
| 1.223 | Cl | SOCH$_3$ | i-C$_3$H$_7$ | H | H | COOCH$_3$ | |
| 1.224 | Cl | SO$_2$CH$_3$ | i-C$_3$H$_7$ | H | H | COOCH$_3$ | |
| 1.225 | SOCH$_3$ | Cl | i-C$_3$H$_7$ | H | H | COOCH$_3$ | |
| 1.226 | SO$_2$CH$_3$ | H | i-C$_3$H$_7$ | H | H | COOCH$_3$ | |
| 1.227 | H | SO$_2$CH$_3$ | i-C$_3$H$_7$ | H | H | COOCH$_3$ | |
| 1.228 | H | CH$_3$ | i-C$_3$H$_7$ | H | H | COOCH$_3$ | |
| 1.229 | Cl | F | i-C$_3$H$_7$ | H | H | COOCH$_3$ | |
| 1.230 | H | CF$_3$ | i-C$_3$H$_7$ | H | H | COOCH$_3$ | |
| 1.231 | F | F | i-C$_3$H$_7$ | H | H | COOCH$_3$ | |
| 1.232 | F | CF$_3$ | i-C$_3$H$_7$ | H | H | COOCH$_3$ | |
| 1.233 | CF$_3$ | F | i-C$_3$H$_7$ | H | H | COOCH$_3$ | |
| 1.234 | H | CCl$_3$ | i-C$_3$H$_7$ | H | H | COOCH$_3$ | |
| 1.235 | CCl$_3$ | H | i-C$_3$H$_7$ | H | H | COOCH$_3$ | |
| 1.236 | Cl | CCl$_3$ | i-C$_3$H$_7$ | H | H | COOCH$_3$ | |
| 1.237 | CCl$_3$ | Cl | i-C$_3$H$_7$ | H | H | COOCH$_3$ | |
| 1.238 | CH$_3$ | H | i-C$_3$H$_7$ | H | H | COOCH$_3$ | |
| 1.239 | Cl | Cl | CH$_3$ | H | H | COOCH$_3$ | |
| 1.240 | Cl | H | CH$_3$ | H | H | COOCH$_3$ | |
| 1.241 | H | Cl | CH$_3$ | H | H | COOCH$_3$ | |
| 1.242 | H | H | CH$_3$ | H | H | COOCH$_3$ | |
| 1.243 | Cl | CF$_3$ | CH$_3$ | H | H | COOCH$_3$ | |
| 1.244 | NO$_2$ | H | CH$_3$ | H | H | COOCH$_3$ | |
| 1.245 | H | NO$_2$ | CH$_3$ | H | H | COOCH$_3$ | |
| 1.246 | NO$_2$ | Cl | CH$_3$ | H | H | COOCH$_3$ | |
| 1.247 | CF$_3$ | H | CH$_3$ | H | H | COOCH$_3$ | |
| 1.248 | H | CF$_3$ | CH$_3$ | H | H | COOCH$_3$ | |
| 1.249 | OCH$_3$ | H | CH$_3$ | H | H | COOCH$_3$ | |
| 1.250 | CN | H | CH$_3$ | H | H | COOCH$_3$ | |
| 1.251 | OCH$_3$ | Cl | CH$_3$ | H | H | COOCH$_3$ | |
| 1.252 | CN | Cl | CH$_3$ | H | H | COOCH$_3$ | |
| 1.253 | Br | Cl | CH$_3$ | H | H | COOCH$_3$ | |
| 1.254 | SCH$_3$ | Cl | CH$_3$ | H | H | COOCH$_3$ | |
| 1.255 | SO$_2$CH$_3$ | Cl | CH$_3$ | H | H | COOCH$_3$ | |
| 1.256 | Cl | SCH$_3$ | CH$_3$ | H | H | COOCH$_3$ | |
| 1.257 | Cl | SOCH$_3$ | CH$_3$ | H | H | COOCH$_3$ | |
| 1.258 | Cl | SO$_2$CH$_3$ | CH$_3$ | H | H | COOCH$_3$ | |
| 1.259 | SOCH$_3$ | Cl | CH$_3$ | H | H | COOCH$_3$ | |
| 1.260 | SO$_2$CH$_3$ | H | CH$_3$ | H | H | COOCH$_3$ | |
| 1.261 | H | SO$_2$CH$_3$ | CH$_3$ | H | H | COOCH$_3$ | |
| 1.262 | H | CH$_3$ | CH$_3$ | H | H | COOCH$_3$ | |
| 1.263 | Cl | F | CH$_3$ | H | H | COOCH$_3$ | |
| 1.264 | H | CF$_3$ | CH$_3$ | H | H | COOCH$_3$ | |
| 1.265 | F | F | CH$_3$ | H | H | COOCH$_3$ | |
| 1.266 | F | CF$_3$ | CH$_3$ | H | H | COOCH$_3$ | |
| 1.267 | CF$_3$ | F | CH$_3$ | H | H | COOCH$_3$ | |
| 1.268 | H | CCl$_3$ | CH$_3$ | H | H | COOCH$_3$ | |
| 1.269 | CCl$_3$ | H | CH$_3$ | H | H | COOCH$_3$ | |
| 1.270 | Cl | CCl$_3$ | CH$_3$ | H | H | COOCH$_3$ | |
| 1.271 | CCl$_3$ | Cl | CH$_3$ | H | H | COOCH$_3$ | |
| 1.272 | CH$_3$ | H | CH$_3$ | H | H | COOCH$_3$ | |
| 1.273 | Cl | Cl | CH$_3$ | CH$_3$ | H | H | m.p. 131–133° C. |
| 1.274 | Cl | H | CH$_3$ | CH$_3$ | H | H | |
| 1.275 | H | Cl | CH$_3$ | CH$_3$ | H | H | |
| 1.276 | H | H | CH$_3$ | CH$_3$ | H | H | |
| 1.277 | Cl | CF$_3$ | CH$_3$ | CH$_3$ | H | H | m.p. 95–98° C. |
| 1.278 | NO$_2$ | H | CH$_3$ | CH$_3$ | H | H | |
| 1.279 | H | NO$_2$ | CH$_3$ | CH$_3$ | H | H | |
| 1.280 | NO$_2$ | Cl | CH$_3$ | CH$_3$ | H | H | |
| 1.281 | CF$_3$ | H | CH$_3$ | CH$_3$ | H | H | |
| 1.282 | H | CF$_3$ | CH$_3$ | CH$_3$ | H | H | |
| 1.283 | OCH$_3$ | H | CH$_3$ | CH$_3$ | H | H | |
| 1.284 | CN | H | CH$_3$ | CH$_3$ | H | H | |
| 1.285 | OCH$_3$ | Cl | CH$_3$ | CH$_3$ | H | H | |
| 1.286 | CN | Cl | CH$_3$ | CH$_3$ | H | H | |
| 1.287 | Br | Cl | CH$_3$ | CH$_3$ | H | H | |
| 1.288 | SCH$_3$ | Cl | CH$_3$ | CH$_3$ | H | H | |
| 1.289 | SO$_2$CH$_3$ | Cl | CH$_3$ | CH$_3$ | H | H | |

TABLE 1-continued

Compounds of formula

[Structure shown with R¹, R², R³, R⁴, R⁵, R⁶ substituents on a bicyclic system with OH, N, and two C=O groups]

| Comp. No. | R¹ | R² | R³ | R⁴ | R⁵ | R⁶ | phys. data |
|---|---|---|---|---|---|---|---|
| 1.290 | Cl | SCH₃ | CH₃ | CH₃ | H | H | |
| 1.291 | Cl | SOCH₃ | CH₃ | CH₃ | H | H | |
| 1.292 | Cl | SO₂CH₃ | CH₃ | CH₃ | H | H | |
| 1.293 | SOCH₃ | Cl | CH₃ | CH₃ | H | H | |
| 1.294 | SO₂CH₃ | H | CH₃ | CH₃ | H | H | |
| 1.295 | H | SO₂CH₃ | CH₃ | CH₃ | H | H | |
| 1.296 | H | CH₃ | CH₃ | CH₃ | H | H | |
| 1.297 | Cl | F | CH₃ | CH₃ | H | H | |
| 1.298 | H | CF₃ | CH₃ | CH₃ | H | H | |
| 1.299 | F | F | CH₃ | CH₃ | H | H | |
| 1.300 | F | CF₃ | CH₃ | CH₃ | H | H | |
| 1.301 | CF₃ | F | CH₃ | CH₃ | H | H | |
| 1.302 | H | CCl₃ | CH₃ | CH₃ | H | H | |
| 1.303 | CCl₃ | H | CH₃ | CH₃ | H | H | |
| 1.304 | Cl | CCl₃ | CH₃ | CH₃ | H | H | |
| 1.305 | CCl₃ | Cl | CH₃ | CH₃ | H | H | |
| 1.306 | CH₃ | H | CH₃ | CH₃ | H | H | |
| 1.307 | Cl | Cl | CH₃ | CH₃ | H | COOC₂H₅ | |
| 1.308 | Cl | H | CH₃ | CH₃ | H | COOC₂H₅ | |
| 1.309 | H | Cl | CH₃ | CH₃ | H | COOC₂H₅ | |
| 1.310 | H | H | CH₃ | CH₃ | H | COOC₂H₅ | |
| 1.311 | Cl | CF₃ | CH₃ | CH₃ | H | COOC₂H₅ | |
| 1.312 | NO₂ | H | CH₃ | CH₃ | H | COOC₂H₅ | |
| 1.313 | H | NO₂ | CH₃ | CH₃ | H | COOC₂H₅ | |
| 1.314 | NO₂ | Cl | CH₃ | CH₃ | H | COOC₂H₅ | |
| 1.315 | CF₃ | H | CH₃ | CH₃ | H | COOC₂H₅ | |
| 1.316 | H | CF₃ | CH₃ | CH₃ | H | COOC₂H₅ | |
| 1.317 | OCH₃ | H | CH₃ | CH₃ | H | COOC₂H₅ | |
| 1.318 | CN | H | CH₃ | CH₃ | H | COOC₂H₅ | |
| 1.319 | OCH₃ | Cl | CH₃ | CH₃ | H | COOC₂H₅ | |
| 1.320 | CN | Cl | CH₃ | CH₃ | H | COOC₂H₅ | |
| 1.321 | Br | Cl | CH₃ | CH₃ | H | COOC₂H₅ | |
| 1.322 | SCH₃ | Cl | CH₃ | CH₃ | H | COOC₂H₅ | |
| 1.323 | SO₂CH₃ | Cl | CH₃ | CH₃ | H | COOC₂H₅ | |
| 1.324 | Cl | SCH₃ | CH₃ | CH₃ | H | COOC₂H₅ | |
| 1.325 | Cl | SOCH₃ | CH₃ | CH₃ | H | COOC₂H₅ | |
| 1.326 | Cl | SO₂CH₃ | CH₃ | CH₃ | H | COOC₂H₅ | |
| 1.327 | SOCH₃ | Cl | CH₃ | CH₃ | H | COOC₂H₅ | |
| 1.328 | SO₂CH₃ | H | CH₃ | CH₃ | H | COOC₂H₅ | |
| 1.329 | H | SO₂CH₃ | CH₃ | CH₃ | H | COOC₂H₅ | |
| 1.330 | H | CH₃ | CH₃ | CH₃ | H | COOC₂H₅ | |
| 1.331 | Cl | F | CH₃ | CH₃ | H | COOC₂H₅ | |
| 1.332 | H | CF₃ | CH₃ | CH₃ | H | COOC₂H₅ | |
| 1.333 | F | F | CH₃ | CH₃ | H | COOC₂H₅ | |
| 1.334 | F | CF₃ | CH₃ | CH₃ | H | COOC₂H₅ | |
| 1.335 | CF₃ | F | CH₃ | CH₃ | H | COOC₂H₅ | |
| 1.336 | H | CCl₃ | CH₃ | CH₃ | H | COOC₂H₅ | |
| 1.337 | CCl₃ | H | CH₃ | CH₃ | H | COOC₂H₅ | |
| 1.338 | Cl | CCl₃ | CH₃ | CH₃ | H | COOC₂H₅ | |
| 1.339 | CCl₃ | Cl | CH₃ | CH₃ | H | COOC₂H₅ | |
| 1.340 | CH₃ | H | CH₃ | CH₃ | H | COOC₂H₅ | |
| 1.341 | Cl | Cl | C₆H₅ | H | H | H | |
| 1.342 | Cl | H | C₆H₅ | H | H | H | |
| 1.343 | H | Cl | C₆H₅ | H | H | H | |
| 1.344 | H | H | C₆H₅ | H | H | H | |
| 1.345 | Cl | CF₃ | C₆H₅ | H | H | H | m.p. >150° C. (decomp.) |
| 1.346 | NO₂ | H | C₆H₅ | H | H | H | |
| 1.347 | H | NO₂ | C₆H₅ | H | H | H | |
| 1.348 | NO₂ | Cl | C₆H₅ | H | H | H | |
| 1.349 | CF₃ | H | C₆H₅ | H | H | H | |
| 1.350 | H | CF₃ | C₆H₅ | H | H | H | |
| 1.351 | OCH₃ | H | C₆H₅ | H | H | H | |
| 1.352 | CN | H | C₆H₅ | H | H | H | |
| 1.353 | OCH₃ | Cl | C₆H₅ | H | H | H | |
| 1.354 | CN | Cl | C₆H₅ | H | H | H | |
| 1.355 | Br | Cl | C₆H₅ | H | H | H | |
| 1.356 | SCH₃ | Cl | C₆H₅ | H | H | H | |

TABLE 1-continued

Compounds of formula

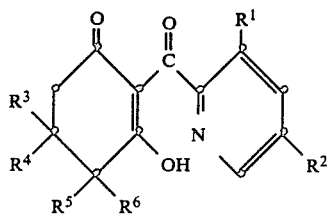

| Comp. No. | $R^1$ | $R^2$ | $R^3$ | $R^4$ | $R^5$ | $R^6$ | phys. data |
|---|---|---|---|---|---|---|---|
| 1.357 | $SO_2CH_3$ | Cl | $C_6H_5$ | H | H | H | |
| 1.358 | Cl | $SCH_3$ | $C_6H_5$ | H | H | H | |
| 1.359 | Cl | $SOCH_3$ | $C_6H_5$ | H | H | H | |
| 1.360 | Cl | $SO_2CH_3$ | $C_6H_5$ | H | H | H | |
| 1.361 | $SOCH_3$ | Cl | $C_6H_5$ | H | H | H | |
| 1.362 | $SO_2CH_3$ | H | $C_6H_5$ | H | H | H | |
| 1.363 | H | $SO_2CH_3$ | $C_6H_5$ | H | H | H | |
| 1.364 | H | $CH_3$ | $C_6H_5$ | H | H | H | |
| 1.365 | Cl | F | $C_6H_5$ | H | H | H | |
| 1.366 | H | $CF_3$ | $C_6H_5$ | H | H | H | |
| 1.367 | F | F | $C_6H_5$ | H | H | H | |
| 1.368 | F | $CF_3$ | $C_6H_5$ | H | H | H | |
| 1.369 | $CF_3$ | F | $C_6H_5$ | H | H | H | |
| 1.370 | H | $CCl_3$ | $C_6H_5$ | H | H | H | |
| 1.371 | $CCl_3$ | H | $C_6H_5$ | H | H | H | |
| 1.372 | Cl | $CCl_3$ | $C_6H_5$ | H | H | H | |
| 1.373 | $CCl_3$ | Cl | $C_6H_5$ | H | H | H | |
| 1.374 | $CH_3$ | H | $C_6H_5$ | H | H | H | |
| 1.375 | Cl | Cl | H | H | $CH_3$ | $CH_3$ | |
| 1.376 | Cl | H | H | H | $CH_3$ | $CH_3$ | |
| 1.377 | H | Cl | H | H | $CH_3$ | $CH_3$ | |
| 1.378 | H | H | H | H | $CH_3$ | $CH_3$ | |
| 1.379 | Cl | $CF_3$ | H | H | $CH_3$ | $CH_3$ | |
| 1.380 | $NO_2$ | H | H | H | $CH_3$ | $CH_3$ | |
| 1.381 | H | $NO_2$ | H | H | $CH_3$ | $CH_3$ | |
| 1.382 | $NO_2$ | Cl | H | H | $CH_3$ | $CH_3$ | |
| 1.383 | $CF_3$ | H | H | H | $CH_3$ | $CH_3$ | |
| 1.384 | H | $CF_3$ | H | H | $CH_3$ | $CH_3$ | |
| 1.385 | $OCH_3$ | H | H | H | $CH_3$ | $CH_3$ | |
| 1.386 | CN | H | H | H | $CH_3$ | $CH_3$ | |
| 1.387 | $OCH_3$ | Cl | H | H | $CH_3$ | $CH_3$ | |
| 1.388 | CN | Cl | H | H | $CH_3$ | $CH_3$ | |
| 1.389 | Br | Cl | H | H | $CH_3$ | $CH_3$ | |
| 1.390 | $SCH_3$ | Cl | H | H | $CH_3$ | $CH_3$ | |
| 1.391 | $SO_2CH_3$ | Cl | H | H | $CH_3$ | $CH_3$ | |
| 1.392 | Cl | $SCH_3$ | H | H | $CH_3$ | $CH_3$ | |
| 1.393 | Cl | $SOCH_3$ | H | H | $CH_3$ | $CH_3$ | |
| 1.394 | Cl | $SO_2CH_3$ | H | H | $CH_3$ | $CH_3$ | |
| 1.395 | $SOCH_3$ | Cl | H | H | $CH_3$ | $CH_3$ | |
| 1.396 | $SO_2CH_3$ | H | H | H | $CH_3$ | $CH_3$ | |
| 1.397 | H | $SO_2CH_3$ | H | H | $CH_3$ | $CH_3$ | |
| 1.398 | H | $CH_3$ | H | H | $CH_3$ | $CH_3$ | |
| 1.399 | Cl | F | H | H | $CH_3$ | $CH_3$ | |
| 1.400 | H | $CF_3$ | H | H | $CH_3$ | $CH_3$ | |
| 1.401 | F | F | H | H | $CH_3$ | $CH_3$ | |
| 1.402 | F | $CF_3$ | H | H | $CH_3$ | $CH_3$ | |
| 1.403 | $CF_3$ | F | H | H | $CH_3$ | $CH_3$ | |
| 1.404 | H | $CCl_3$ | H | H | $CH_3$ | $CH_3$ | |
| 1.405 | $CCl_3$ | H | H | H | $CH_3$ | $CH_3$ | |
| 1.406 | Cl | $CCl_3$ | H | H | $CH_3$ | $CH_3$ | |
| 1.407 | $CCl_3$ | Cl | H | H | $CH_3$ | $CH_3$ | |
| 1.408 | $CH_3$ | H | H | H | $CH_3$ | $CH_3$ | |
| 1.409 | Cl | Cl | $C_6H_5-CH_2-$ | H | H | H | |
| 1.410 | Cl | H | $C_6H_5-CH_2-$ | H | H | H | |
| 1.411 | H | Cl | $C_6H_5-CH_2-$ | H | H | H | |
| 1.412 | H | H | $C_6H_5-CH_2-$ | H | H | H | |
| 1.413 | Cl | $CF_3$ | $C_6H_5-CH_2-$ | H | H | H | |
| 1.414 | $NO_2$ | H | $C_6H_5-CH_2-$ | H | H | H | |
| 1.415 | H | $NO_2$ | $C_6H_5-CH_2-$ | H | H | H | |
| 1.416 | $NO_2$ | Cl | $C_6H_5-CH_2-$ | H | H | H | |
| 1.417 | $CF_3$ | H | $C_6H_5-CH_2-$ | H | H | H | |
| 1.418 | H | $CF_3$ | $C_6H_5-CH_2-$ | H | H | H | |
| 1.419 | $OCH_3$ | H | $C_6H_5-CH_2-$ | H | H | H | |
| 1.420 | CN | H | $C_6H_5-CH_2-$ | H | H | H | |
| 1.421 | $OCH_3$ | Cl | $C_6H_5-CH_2-$ | H | H | H | |
| 1.422 | CN | Cl | $C_6H_5-CH_2-$ | H | H | H | |
| 1.423 | Br | Cl | $C_6H_5-CH_2-$ | H | H | H | |
| 1.424 | $SCH_3$ | Cl | $C_6H_5-CH_2-$ | H | H | H | |

TABLE 1-continued

Compounds of formula

| Comp. No. | $R^1$ | $R^2$ | $R^3$ | $R^4$ | $R^5$ | $R^6$ | phys. data |
|---|---|---|---|---|---|---|---|
| 1.425 | $SO_2CH_3$ | Cl | $C_6H_5-CH_2-$ | H | H | H | |
| 1.426 | Cl | $SCH_3$ | $C_6H_5-CH_2-$ | H | H | H | |
| 1.427 | Cl | $SOCH_3$ | $C_6H_5-CH_2-$ | H | H | H | |
| 1.428 | Cl | $SO_2CH_3$ | $C_6H_5-CH_2-$ | H | H | H | |
| 1.429 | $SOCH_3$ | Cl | $C_6H_5-CH_2-$ | H | H | H | |
| 1.430 | $SO_2CH_3$ | H | $C_6H_5-CH_2-$ | H | H | H | |
| 1.431 | H | $SO_2CH_3$ | $C_6H_5-CH_2-$ | H | H | H | |
| 1.432 | H | $CH_3$ | $C_6H_5-CH_2-$ | H | H | H | |
| 1.433 | Cl | F | $C_6H_5-CH_2-$ | H | H | H | |
| 1.434 | H | $CF_3$ | $C_6H_5-CH_2-$ | H | H | H | |
| 1.435 | F | F | $C_6H_5-CH_2-$ | H | H | H | |
| 1.436 | F | $CF_3$ | $C_6H_5-CH_2-$ | H | H | H | |
| 1.437 | $CF_3$ | F | $C_6H_5-CH_2-$ | H | H | H | |
| 1.438 | H | $CCl_3$ | $C_6H_5-CH_2-$ | H | H | H | |
| 1.439 | $CCl_3$ | H | $C_6H_5-CH_2-$ | H | H | H | |
| 1.440 | Cl | $CCl_3$ | $C_6H_5-CH_2-$ | H | H | H | |
| 1.441 | $CCl_3$ | Cl | $C_6H_5-CH_2-$ | H | H | H | |
| 1.442 | $CH_3$ | H | $C_6H_5-CH_2-$ | H | H | H | |
| 1.443 | Cl | Cl | $4-Cl-C_6H_4$ | H | H | H | |
| 1.444 | Cl | H | $4-Cl-C_6H_4$ | H | H | H | |
| 1.445 | H | Cl | $4-Cl-C_6H_4$ | H | H | H | |
| 1.446 | H | H | $4-Cl-C_6H_4$ | H | H | H | |
| 1.447 | Cl | $CF_3$ | $4-Cl-C_6H_4$ | H | H | H | |
| 1.448 | $NO_2$ | H | $4-Cl-C_6H_4$ | H | H | H | |
| 1.449 | H | $NO_2$ | $4-Cl-C_6H_4$ | H | H | H | |
| 1.450 | $NO_2$ | Cl | $4-Cl-C_6H_4$ | H | H | H | |
| 1.451 | $CF_3$ | H | $4-Cl-C_6H_4$ | H | H | H | |
| 1.452 | H | $CF_3$ | $4-Cl-C_6H_4$ | H | H | H | |
| 1.453 | $OCH_3$ | H | $4-Cl-C_6H_4$ | H | H | H | |
| 1.454 | CN | H | $4-Cl-C_6H_4$ | H | H | H | |
| 1.455 | $OCH_3$ | Cl | $4-Cl-C_6H_4$ | H | H | H | |
| 1.456 | CN | Cl | $4-Cl-C_6H_4$ | H | H | H | |
| 1.457 | Br | Cl | $4-Cl-C_6H_4$ | H | H | H | |
| 1.458 | $SCH_3$ | Cl | $4-Cl-C_6H_4$ | H | H | H | |
| 1.459 | $SO_2CH_3$ | Cl | $4-Cl-C_6H_4$ | H | H | H | |
| 1.460 | Cl | $SCH_3$ | $4-Cl-C_6H_4$ | H | H | H | |
| 1.461 | Cl | $SOCH_3$ | $4-Cl-C_6H_4$ | H | H | H | |
| 1.462 | Cl | $SO_2CH_3$ | $4-Cl-C_6H_4$ | H | H | H | |
| 1.463 | $SOCH_3$ | Cl | $4-Cl-C_6H_4$ | H | H | H | |
| 1.464 | $SO_2CH_3$ | H | $4-Cl-C_6H_4$ | H | H | H | |
| 1.465 | H | $SO_2CH_3$ | $4-Cl-C_6H_4$ | H | H | H | |
| 1.466 | H | $CH_3$ | $4-Cl-C_6H_4$ | H | H | H | |
| 1.467 | Cl | F | $4-Cl-C_6H_4$ | H | H | H | |
| 1.468 | H | $CF_3$ | $4-Cl-C_6H_4$ | H | H | H | |
| 1.469 | F | F | $4-Cl-C_6H_4$ | H | H | H | |
| 1.470 | F | $CF_3$ | $4-Cl-C_6H_4$ | H | H | H | |
| 1.471 | $CF_3$ | F | $4-Cl-C_6H_4$ | H | H | H | |
| 1.472 | H | $CCl_3$ | $4-Cl-C_6H_4$ | H | H | H | |
| 1.473 | $CCl_3$ | H | $4-Cl-C_6H_4$ | H | H | H | |
| 1.474 | Cl | $CCl_3$ | $4-Cl-C_6H_4$ | H | H | H | |
| 1.475 | $CCl_3$ | Cl | $4-Cl-C_6H_4$ | H | H | H | |
| 1.476 | $CH_3$ | H | $4-Cl-C_6H_4$ | H | H | H | |
| 1.477 | Cl | Cl | $CH_3$ | H | $CH_3$ | H | |
| 1.478 | Cl | H | $CH_3$ | H | $CH_3$ | H | |
| 1.479 | H | Cl | $CH_3$ | H | $CH_3$ | H | |
| 1.480 | H | H | $CH_3$ | H | $CH_3$ | H | |
| 1.481 | Cl | $CF_3$ | $CH_3$ | H | $CH_3$ | H | |
| 1.482 | $NO_2$ | H | $CH_3$ | H | $CH_3$ | H | |
| 1.483 | H | $NO_2$ | $CH_3$ | H | $CH_3$ | H | |
| 1.484 | $NO_2$ | Cl | $CH_3$ | H | $CH_3$ | H | |
| 1.485 | $CF_3$ | H | $CH_3$ | H | $CH_3$ | H | |
| 1.486 | H | $CF_3$ | $CH_3$ | H | $CH_3$ | H | |
| 1.487 | $OCH_3$ | H | $CH_3$ | H | $CH_3$ | H | |
| 1.488 | CN | H | $CH_3$ | H | $CH_3$ | H | |
| 1.489 | $OCH_3$ | Cl | $CH_3$ | H | $CH_3$ | H | |
| 1.490 | CN | Cl | $CH_3$ | H | $CH_3$ | H | |
| 1.491 | Br | Cl | $CH_3$ | H | $CH_3$ | H | |
| 1.492 | $SCH_3$ | Cl | $CH_3$ | H | $CH_3$ | H | |

TABLE 1-continued

Compounds of formula

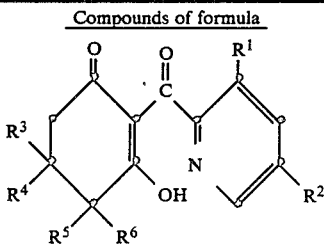

| Comp. No. | R¹ | R² | R³ | R⁴ | R⁵ | R⁶ | phys. data |
|---|---|---|---|---|---|---|---|
| 1.493 | SO₂CH₃ | Cl | CH₃ | H | CH₃ | H | |
| 1.494 | Cl | SCH₃ | CH₃ | H | CH₃ | H | |
| 1.495 | Cl | SOCH₃ | CH₃ | H | CH₃ | H | |
| 1.496 | Cl | SO₂CH₃ | CH₃ | H | CH₃ | H | |
| 1.497 | SOCH₃ | Cl | CH₃ | H | CH₃ | H | |
| 1.498 | SO₂CH₃ | H | CH₃ | H | CH₃ | H | |
| 1.499 | H | SO₂CH₃ | CH₃ | H | CH₃ | H | |
| 1.500 | H | CH₃ | CH₃ | H | CH₃ | H | |
| 1.501 | Cl | F | CH₃ | H | CH₃ | H | |
| 1.502 | H | CF₃ | CH₃ | H | CH₃ | H | |
| 1.503 | F | F | CH₃ | H | CH₃ | H | |
| 1.504 | F | CF₃ | CH₃ | H | CH₃ | H | |
| 1.505 | CF₃ | F | CH₃ | H | CH₃ | H | |
| 1.506 | H | CCl₃ | CH₃ | H | CH₃ | H | |
| 1.507 | CCl₃ | H | CH₃ | H | CH₃ | H | |
| 1.508 | Cl | CCl₃ | CH₃ | H | CH₃ | H | |
| 1.509 | CCl₃ | Cl | CH₃ | H | CH₃ | H | |
| 1.510 | CH₃ | H | CH₃ | H | CH₃ | H | |
| 1.511 | Cl | Cl | H | H | H | CN | |
| 1.512 | Cl | H | H | H | H | CN | |
| 1.513 | H | Cl | H | H | H | CN | |
| 1.514 | H | H | H | H | H | CN | |
| 1.515 | Cl | CF₃ | H | H | H | CN | |
| 1.516 | NO₂ | H | H | H | H | CN | |
| 1.517 | H | NO₂ | H | H | H | CN | |
| 1.518 | NO₂ | Cl | H | H | H | CN | |
| 1.519 | CF₃ | H | H | H | H | CN | |
| 1.520 | H | CF₃ | H | H | H | CN | |
| 1.521 | OCH₃ | H | H | H | H | CN | |
| 1.522 | CN | H | H | H | H | CN | |
| 1.523 | OCH₃ | Cl | H | H | H | CN | |
| 1.524 | CN | Cl | H | H | H | CN | |
| 1.525 | Br | Cl | H | H | H | CN | |
| 1.526 | SCH₃ | Cl | H | H | H | CN | |
| 1.527 | SO₂CH₃ | Cl | H | H | H | CN | |
| 1.528 | Cl | SCH₃ | H | H | H | CN | |
| 1.529 | Cl | SOCH₃ | H | H | H | CN | |
| 1.530 | Cl | SO₂CH₃ | H | H | H | CN | |
| 1.531 | SOCH₃ | Cl | H | H | H | CN | |
| 1.532 | SO₂CH₃ | H | H | H | H | CN | |
| 1.533 | H | SO₂CH₃ | H | H | H | CN | |
| 1.534 | H | CH₃ | H | H | H | CN | |
| 1.535 | Cl | F | H | H | H | CN | |
| 1.536 | H | CF₃ | H | H | H | CN | |
| 1.537 | F | F | H | H | H | CN | |
| 1.538 | F | CF₃ | H | H | H | CN | |
| 1.539 | CF₃ | F | H | H | H | CN | |
| 1.540 | H | CCl₃ | H | H | H | CN | |
| 1.541 | CCl₃ | H | H | H | H | CN | |
| 1.542 | Cl | CCl₃ | H | H | H | CN | |
| 1.543 | CCl₃ | Cl | H | H | H | CN | |
| 1,544 | CH₃ | H | H | H | H | CN | |
| 1.545 | Cl | Cl | CH₃ | H | H | CN | |
| 1.546 | Cl | H | CH₃ | H | H | CN | |
| 1.547 | H | Cl | CH₃ | H | H | CN | |
| 1.548 | H | H | CH₃ | H | H | CN | |
| 1.549 | Cl | CF₃ | CH₃ | H | H | CN | |
| 1.550 | NO₂ | H | CH₃ | H | H | CN | |
| 1.551 | H | NO₂ | CH₃ | H | H | CN | |
| 1.552 | NO₂ | Cl | CH₃ | H | H | CN | |
| 1.553 | CF₃ | H | CH₃ | H | H | CN | |
| 1.554 | H | CF₃ | CH₃ | H | H | CN | |
| 1.555 | OCH₃ | H | CH₃ | H | H | CN | |
| 1.556 | CN | H | CH₃ | H | H | CN | |
| 1.557 | OCH₃ | Cl | CH₃ | H | H | CN | |
| 1.558 | CN | Cl | CH₃ | H | H | CN | |
| 1.559 | Br | Cl | CH₃ | H | H | CN | |
| 1.560 | SCH₃ | Cl | CH₃ | H | H | CN | |

TABLE 1-continued

Compounds of formula

| Comp. No. | $R^1$ | $R^2$ | $R^3$ | $R^4$ | $R^5$ | $R^6$ | phys. data |
|---|---|---|---|---|---|---|---|
| 1.561 | $SO_2CH_3$ | Cl | $CH_3$ | H | H | CN | |
| 1.562 | Cl | $SCH_3$ | $CH_3$ | H | H | CN | |
| 1.563 | Cl | $SOCH_3$ | $CH_3$ | H | H | CN | |
| 1.564 | Cl | $SO_2CH_3$ | $CH_3$ | H | H | CN | |
| 1.565 | $SOCH_3$ | Cl | $CH_3$ | H | H | CN | |
| 1.566 | $SO_2CH_3$ | H | $CH_3$ | H | H | CN | |
| 1.567 | H | $SO_2CH_3$ | $CH_3$ | H | H | CN | |
| 1.568 | H | $CH_3$ | $CH_3$ | H | H | CN | |
| 1.569 | Cl | F | $CH_3$ | H | H | CN | |
| 1.570 | H | $CF_3$ | $CH_3$ | H | H | CN | |
| 1.571 | F | F | $CH_3$ | H | H | CN | |
| 1.572 | F | $CF_3$ | $CH_3$ | H | H | CN | |
| 1.573 | $CF_3$ | F | $CH_3$ | H | H | CN | |
| 1.574 | H | $CCl_3$ | $CH_3$ | H | H | CN | |
| 1.575 | $CCl_3$ | H | $CH_3$ | H | H | CN | |
| 1.576 | Cl | $CCl_3$ | $CH_3$ | H | H | CN | |
| 1.577 | $CCl_3$ | Cl | $CH_3$ | H | H | CN | |
| 1.578 | $CH_3$ | H | $CH_3$ | H | H | CN | |
| 1.579 | Cl | Cl | $C_6H_5$ | H | H | $COOCH_3$ | |
| 1.580 | Cl | H | $C_6H_5$ | H | H | $COOCH_3$ | |
| 1.581 | H | Cl | $C_6H_5$ | H | H | $COOCH_3$ | |
| 1.582 | H | H | $C_6H_5$ | H | H | $COOCH_3$ | |
| 1.583 | Cl | $CF_3$ | $C_6H_5$ | H | H | $COOCH_3$ | m.p. >180 decomp. |
| 1.584 | $NO_2$ | H | $C_6H_5$ | H | H | $COOCH_3$ | |
| 1.585 | H | $NO_2$ | $C_6H_5$ | H | H | $COOCH_3$ | |
| 1.586 | $NO_2$ | Cl | $C_6H_5$ | H | H | $COOCH_3$ | |
| 1.587 | $CF_3$ | H | $C_6H_5$ | H | H | $COOCH_3$ | |
| 1.588 | H | $CF_3$ | $C_6H_5$ | H | H | $COOCH_3$ | |
| 1.589 | $OCH_3$ | H | $C_6H_5$ | H | H | $COOCH_3$ | |
| 1.590 | CN | H | $C_6H_5$ | H | H | $COOCH_3$ | |
| 1.591 | $OCH_3$ | Cl | $C_6H_5$ | H | H | $COOCH_3$ | |
| 1.592 | CN | Cl | $C_6H_5$ | H | H | $COOCH_3$ | |
| 1.593 | Br | Cl | $C_6H_5$ | H | H | $COOCH_3$ | |
| 1.594 | $SCH_3$ | Cl | $C_6H_5$ | H | H | $COOCH_3$ | |
| 1.595 | $SO_2CH_3$ | Cl | $C_6H_5$ | H | H | $COOCH_3$ | |
| 1.596 | Cl | $SCH_3$ | $C_6H_5$ | H | H | $COOCH_3$ | |
| 1.597 | Cl | $SOCH_3$ | $C_6H_5$ | H | H | $COOCH_3$ | |
| 1.598 | Cl | $SO_2CH_3$ | $C_6H_5$ | H | H | $COOCH_3$ | |
| 1.599 | $SOCH_3$ | Cl | $C_6H_5$ | H | H | $COOCH_3$ | |
| 1.600 | $SO_2CH_3$ | H | $C_6H_5$ | H | H | $COOCH_3$ | |
| 1.601 | H | $SO_2CH_3$ | $C_6H_5$ | H | H | $COOCH_3$ | |
| 1.602 | H | $CH_3$ | $C_6H_5$ | H | H | $COOCH_3$ | |
| 1.603 | Cl | F | $C_6H_5$ | H | H | $COOCH_3$ | |
| 1.604 | H | $CF_3$ | $C_6H_5$ | H | H | $COOCH_3$ | |
| 1.605 | F | F | $C_6H_5$ | H | H | $COOCH_3$ | |
| 1.606 | F | $CF_3$ | $C_6H_5$ | H | H | $COOCH_3$ | |
| 1.607 | $CF_3$ | F | $C_6H_5$ | H | H | $COOCH_3$ | |
| 1.608 | H | $CCl_3$ | $C_6H_5$ | H | H | $COOCH_3$ | |
| 1.609 | $CCl_3$ | H | $C_6H_5$ | H | H | $COOCH_3$ | |
| 1.610 | Cl | $CCl_3$ | $C_6H_5$ | H | H | $COOCH_3$ | |
| 1.611 | $CCl_3$ | Cl | $C_6H_5$ | H | H | $COOCH_3$ | |
| 1.612 | $CH_3$ | H | $C_6H_5$ | H | H | $COOCH_3$ | |
| 1.613 | H | $SCH_3$ | H | H | H | H | m.p. >140° Z |
| 1.614 | H | $SOCH_3$ | H | H | H | H | |
| 1.615 | H | $SO_2CH_3$ | H | H | H | H | |
| 1.616 | $CO_2H$ | H | H | H | H | H | m.p. >150° Z |
| 1.617 | $CO_2H$ | H | $CH_3$ | H | H | H | |
| 1.618 | $CO_2H$ | H | H | $C_3H_7(i)$ | H | H | |
| 1.619 | $CO_2H$ | H | H | Phenyl | H | H | |
| 1.620 | $CO_2CH_3$ | H | H | H | H | H | |
| 1.621 | $CO_2C_2H_5$ | H | H | H | H | H | |
| 1.622 | $CO_2NH_2$ | H | H | H | H | H | |
| 1.623 | CN | H | H | H | H | H | |
| 1.624 | $CO_2H$ | $CH_3$ | H | H | H | H | |
| 1.625 | $CO_2CH_3$ | $CH_3$ | H | H | H | H | |
| 1.626 | $CO_2H$ | $C_2H_5$ | H | H | H | H | |
| 1.627 | $CO_2CH_3$ | $C_2H_5$ | H | H | H | H | |
| 1.628 | $CO_2CH_3$ | Br | H | H | H | H | |

TABLE 1-continued

Compounds of formula

| Comp. No. | R¹ | R² | R³ | R⁴ | R⁵ | R⁶ | phys. data |
|---|---|---|---|---|---|---|---|
| 1.629 | $CO_2H$ | Br | H | H | H | H | |
| 1.630 | Cl | $CF_3$ | $CH_3$ | $CH_3$ | $CH_3$ | H | m.p. 65-70° C. |
| 1.631 | H | $CF_3$ | $CH_3$ | $CH_3$ | $CH_3$ | H | |
| 1.632 | Cl | $OCH_3$ | H | H | H | H | |
| 1.633 | Cl | $SC_2H_5$ | H | H | H | H | |
| 1.634 | Cl | $SOC_2H_5$ | H | H | H | H | |
| 1.635 | Cl | $SO_2C_2H_5$ | H | H | H | H | |
| 1.636 | $SC_2H_5$ | Cl | H | H | H | H | |
| 1.637 | $SOC_2H_5$ | Cl | H | H | H | H | |
| 1.638 | $SO_2C_2H_5$ | Cl | H | H | H | H | |
| 1.639 | H | $SO_2C_2H_5$ | H | H | H | H | |
| 1.640 | Cl | $SO_2C_3H_7(i)$ | H | H | H | H | |
| 1.641 | Cl | $SOC_3H_7(i)$ | H | H | H | H | |
| 1.642 | Cl | $SC_3H_7(i)$ | H | H | H | H | |
| 1.643 | Cl | $OCH_3$ | H | H | H | H | |
| 1.644 | Cl | $OC_3H_7(i)$ | H | H | H | H | |
| 1.645 | Cl | Br | H | H | H | H | |
| 1.646 | H | $OCH_3$ | H | H | H | H | m.p. 79-85° C. |

P.1.2. Preparation of salts of formula I

P.1.2.1. Sodium salt of 2-(3-chloro-5-trifluoromethyl-pyridin-2-ylcarbonyl) -cyclohex-1-en1-ol-3one 3.222 g of 2-(3-chloro-5-trifluoromethylpyridin-2-ylcarbonyl)-cyclohex-1-en-1-ol-3-one are dissolved in 20 ml of methanol, 0.54 g of sodium methoxide is added and the whole is stirred at room temperature for 15 minutes and then concentrated to dryness on a rotary evaporator. The residue is triturated with diethyl ether, filtered and dried.

The title compound of formula

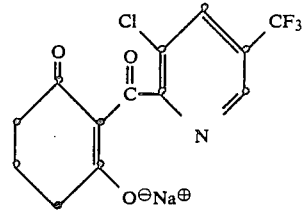

is isolated in quantitative yield in the form of a colourless solid (Compound No. 2.006).

The salts of Table 2 can be synthesised analogously to the above preparation processes.

TABLE 2

Compounds of formula

| Comp. No. | R¹ | R² | R³ | R⁴ | R⁵ | R⁶ | M⊕ | phys. data |
|---|---|---|---|---|---|---|---|---|
| 2.001 | Cl | Cl | H | H | H | H | $Na^\oplus$ | |
| 2.002 | Cl | Cl | H | H | H | H | $Li^\oplus$ | |
| 2.003 | Cl | Cl | H | H | H | H | $\frac{1}{2}Ca^{2\oplus}$ | |
| 2.004 | Cl | Cl | H | H | H | H | $NH(CH_3)_3^\oplus$ | |
| 2.005 | Cl | Cl | H | H | H | H | $NH(C_2H_5OH)_3^\oplus$ | |
| 2.006 | Cl | $CF_3$ | H | H | H | H | $Na^\oplus$ | colourless solid |
| 2.007 | Cl | $CF_3$ | H | H | H | H | $Li^\oplus$ | |
| 2.008 | Cl | $CF_3$ | H | H | H | H | $\frac{1}{2}Ca^{2\oplus}$ | |
| 2.009 | Cl | $CF_3$ | H | H | H | H | $NH(CH_3)_3^\oplus$ | |
| 2.010 | Cl | $CF_3$ | H | H | H | H | $NH(C_2H_5OH)_3^\oplus$ | |
| 2.011 | $NO_2$ | H | H | H | H | H | $Na^\oplus$ | |
| 2.012 | $NO_2$ | H | H | H | H | H | $Li^\oplus$ | |
| 2.013 | $NO_2$ | H | H | H | H | H | $\frac{1}{2}Ca^{2\oplus}$ | |
| 2.014 | $NO_2$ | H | H | H | H | H | $NH(CH_3)_3^\oplus$ | |
| 2.015 | $NO_2$ | H | H | H | H | H | $NH(C_2H_5OH)_3^\oplus$ | |
| 2.016 | H | $NO_2$ | H | H | H | H | $Na^\oplus$ | |

TABLE 2-continued

Compounds of formula

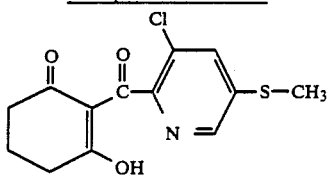

| Comp. No. | R¹ | R² | R³ | R⁴ | R⁵ | R⁶ | M⊕ | phys. data |
|---|---|---|---|---|---|---|---|---|
| 2.017 | H | NO₂ | H | H | H | H | Li⊕ | |
| 2.018 | H | NO₂ | H | H | H | H | ½Ca²⊕ | |
| 2.019 | H | NO₂ | H | H | H | H | NH(CH₃)₃⊕ | |
| 2.020 | H | NO₂ | H | H | H | H | NH(C₂H₅OH)₃⊕ | |
| 2.021 | H | H | H | H | H | H | Na⊕ | |
| 2.022 | H | H | H | H | H | H | Li⊕ | |
| 2.023 | H | H | H | H | H | H | ½Ca²⊕ | |
| 2.024 | H | H | H | H | H | H | NH(CH₃)₃⊕ | |
| 2.025 | H | H | H | H | H | H | NH(C₂H₅OH)₃⊕ | |
| 2.026 | Cl | CCl₃ | H | H | H | H | Na⊕ | |
| 2.027 | Cl | CCl₃ | H | H | H | H | Li⊕ | |
| 2.028 | Cl | CCl₃ | H | H | H | H | ½Ca²⊕ | |
| 2.029 | Cl | CCl₃ | H | H | H | H | NH(CH₃)₃⊕ | |
| 2.030 | Cl | CCl₃ | H | H | H | H | NH(C₂H₅OH)₃⊕ | |
| 2.031 | F | CF₃ | H | H | H | H | Na⊕ | |
| 2.032 | F | CF₃ | H | H | H | H | Li⊕ | |
| 2.033 | F | CF₃ | H | H | H | H | ½Ca²⊕ | |
| 2.034 | F | CF₃ | H | H | H | H | NH(CH₃)₃⊕ | |
| 2.035 | F | CF₃ | H | H | H | H | NH(C₂H₅OH)₃⊕ | |
| 2.036 | Cl | Cl | CH₃ | H | H | H | Na⊕ | |
| 2.037 | Cl | Cl | CH₃ | H | H | H | Li⊕ | |
| 2.038 | Cl | Cl | CH₃ | H | H | H | ½Ca²⊕ | |
| 2.039 | Cl | Cl | CH₃ | H | H | H | NH(CH₃)₃⊕ | |
| 2.040 | Cl | Cl | CH₃ | H | H | H | NH(C₂H₅OH)₃⊕ | |
| 2.041 | Cl | CF₃ | CH₃ | H | H | H | Na⊕ | |
| 2.042 | Cl | CF₃ | CH₃ | H | H | H | Li⊕ | |
| 2.043 | Cl | CF₃ | CH₃ | H | H | H | ½Ca²⊕ | |
| 2.044 | Cl | CF₃ | CH₃ | H | H | H | NH(CH₃)₃⊕ | |
| 2.045 | Cl | CF₃ | CH₃ | H | H | H | NH(C₂H₅OH)₃⊕ | |
| 2.046 | NO₂ | H | CH₃ | H | H | H | Na⊕ | |
| 2.047 | NO₂ | H | CH₃ | H | H | H | Li⊕ | |
| 2.048 | NO₂ | H | CH₃ | H | H | H | ½Ca²⊕ | |
| 2.049 | NO₂ | H | CH₃ | H | H | H | NH(CH₃)₃⊕ | |
| 2.050 | NO₂ | H | CH₃ | H | H | H | NH(C₂H₅OH)₃⊕ | |
| 2.051 | H | NO₂ | CH₃ | H | H | H | Na⊕ | |
| 2.052 | H | NO₂ | CH₃ | H | H | H | Li⊕ | |
| 2.053 | H | NO₂ | CH₃ | H | H | H | ½Ca²⊕ | |
| 2.054 | H | NO₂ | CH₃ | H | H | H | NH(CH₃)₃⊕ | |
| 2.055 | H | NO₂ | CH₃ | H | H | H | NH(C₂H₅OH)₃⊕ | |
| 2.056 | H | H | CH₃ | H | H | H | Na⊕ | |
| 2.057 | H | H | CH₃ | H | H | H | Li⊕ | |
| 2.058 | H | H | CH₃ | H | H | H | ½Ca²⊕ | |
| 2.059 | H | H | CH₃ | H | H | H | NH(CH₃)₃⊕ | |
| 2.060 | H | H | CH₃ | H | H | H | NH(C₂H₅OH)₃⊕ | |
| 2.061 | Cl | CCl₃ | CH₃ | H | H | H | Na⊕ | |
| 2.062 | Cl | CCl₃ | CH₃ | H | H | H | Li⊕ | |
| 2.063 | Cl | CCl₃ | CH₃ | H | H | H | ½Ca²⊕ | |
| 2.064 | Cl | CCl₃ | CH₃ | H | H | H | NH(CH₃)₃⊕ | |
| 2.065 | Cl | CCl₃ | CH₃ | H | H | H | NH(C₂H₅OH)₃⊕ | |
| 2.066 | F | CF₃ | CH₃ | H | H | H | Na⊕ | |
| 2.067 | F | CF₃ | CH₃ | H | H | H | Li⊕ | |
| 2.068 | F | CF₃ | CH₃ | H | H | H | ½Ca²⊕ | |
| 2.069 | F | CF₃ | CH₃ | H | H | H | NH(CH₃)₃⊕ | |
| 2.070 | F | CF₃ | CH₃ | H | H | H | NH(C₂H₅OH)₃⊕ | |
| 2.071 | Cl | Cl | n-C₃H₇ | H | H | H | Na⊕ | |
| 2.072 | Cl | Cl | n-C₃H₇ | H | H | H | Li⊕ | |
| 2.073 | Cl | Cl | n-C₃H₇ | H | H | H | ½Ca²⊕ | |
| 2.074 | Cl | Cl | n-C₃H₇ | H | H | H | NH(CH₃)₃⊕ | |
| 2.075 | Cl | Cl | n-C₃H₇ | H | H | H | NH(C₂H₅OH)₃⊕ | |
| 2.076 | Cl | CF₃ | n-C₃H₇ | H | H | H | Na⊕ | |
| 2.077 | Cl | CF₃ | n-C₃H₇ | H | H | H | Li⊕ | |
| 2.078 | Cl | CF₃ | n-C₃H₇ | H | H | H | ½Ca²⊕ | |
| 2.079 | Cl | CF₃ | n-C₃H₇ | H | H | H | NH(CH₃)₃⊕ | |
| 2.080 | Cl | CF₃ | n-C₃H₇ | H | H | H | NH(C₂H₅OH)₃⊕ | |
| 2.081 | NO₂ | H | n-C₃H₇ | H | H | H | Na⊕ | |
| 2.082 | NO₂ | H | n-C₃H₇ | H | H | H | Li⊕ | |
| 2.083 | NO₂ | H | n-C₃H₇ | H | H | H | ½Ca²⊕ | |
| 2.084 | NO₂ | H | n-C₃H₇ | H | H | H | NH(CH₃)₃⊕ | |
| 2.085 | NO₂ | H | n-C₃H₇ | H | H | H | NH(C₂H₅OH)₃⊕ | |
| 2.086 | H | NO₂ | n-C₃H₇ | H | H | H | Na⊕ | |

TABLE 2-continued

Compounds of formula

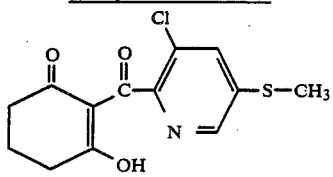

| Comp. No. | R¹ | R² | R³ | R⁴ | R⁵ | R⁶ | M⊕ | phys. data |
|---|---|---|---|---|---|---|---|---|
| 2.087 | H | NO$_2$ | n-C$_3$H$_7$ | H | H | H | Li⊕ | |
| 2.088 | H | NO$_2$ | n-C$_3$H$_7$ | H | H | H | ½Ca$^{2⊕}$ | |
| 2.089 | H | NO$_2$ | n-C$_3$H$_7$ | H | H | H | NH(CH$_3$)$_3$⊕ | |
| 2.090 | H | NO$_2$ | n-C$_3$H$_7$ | H | H | H | NH(C$_2$H$_5$OH)$_3$⊕ | |
| 2.091 | H | H | n-C$_3$H$_7$ | H | H | H | Na⊕ | |
| 2.092 | H | H | n-C$_3$H$_7$ | H | H | H | Li⊕ | |
| 2.093 | H | H | n-C$_3$H$_7$ | H | H | H | ½Ca$^{2⊕}$ | |
| 2.094 | H | H | n-C$_3$H$_7$ | H | H | H | NH(CH$_3$)$_3$⊕ | |
| 2.095 | H | H | n-C$_3$H$_7$ | H | H | H | NH(C$_2$H$_5$OH)$_3$⊕ | |
| 2.096 | Cl | CCl$_3$ | n-C$_3$H$_7$ | H | H | H | Na⊕ | |
| 2.097 | Cl | CCl$_3$ | n-C$_3$H$_7$ | H | H | H | Li⊕ | |
| 2.098 | Cl | CCl$_3$ | n-C$_3$H$_7$ | H | H | H | ½Ca$^{2⊕}$ | |
| 2.099 | Cl | CCl$_3$ | n-C$_3$H$_7$ | H | H | H | NH(CH$_3$)$_3$⊕ | |
| 2.100 | Cl | CCl$_3$ | n-C$_3$H$_7$ | H | H | H | NH(C$_2$H$_5$OH)$_3$⊕ | |
| 2.101 | F | CF$_3$ | n-C$_3$H$_7$ | H | H | H | Na⊕ | |
| 2.102 | F | CF$_3$ | n-C$_3$H$_7$ | H | H | H | Li⊕ | |
| 2.103 | F | CF$_3$ | n-C$_3$H$_7$ | H | H | H | ½Ca$^{2⊕}$ | |
| 2.104 | F | CF$_3$ | n-C$_3$H$_7$ | H | H | H | NH(CH$_3$)$_3$⊕ | |
| 2.105 | F | CF$_3$ | n-C$_3$H$_7$ | H | H | H | NH(C$_2$H$_5$OH)$_3$⊕ | |
| 2.106 | Cl | Cl | i-C$_3$H$_7$ | H | H | H | Na⊕ | |
| 2.107 | Cl | Cl | i-C$_3$H$_7$ | H | H | H | Li⊕ | |
| 2.108 | Cl | Cl | i-C$_3$H$_7$ | H | H | H | ½Ca$^{2⊕}$ | |
| 2.109 | Cl | Cl | i-C$_3$H$_7$ | H | H | H | NH(CH$_3$)$_3$⊕ | |
| 2.110 | Cl | Cl | i-C$_3$H$_7$ | H | H | H | NH(C$_2$H$_5$OH)$_3$⊕ | |
| 2.111 | Cl | CF$_3$ | i-C$_3$H$_7$ | H | H | H | Na⊕ | |
| 2.112 | Cl | CF$_3$ | i-C$_3$H$_7$ | H | H | H | Li⊕ | |
| 2.113 | Cl | CF$_3$ | i-C$_3$H$_7$ | H | H | H | ½Ca$^{2⊕}$ | |
| 2.114 | Cl | CF$_3$ | i-C$_3$H$_7$ | H | H | H | NH(CH$_3$)$_3$⊕ | |
| 2.115 | Cl | CF$_3$ | i-C$_3$H$_7$ | H | H | H | NH(C$_2$H$_5$OH)$_3$⊕ | |
| 2.116 | NO$_2$ | H | i-C$_3$H$_7$ | H | H | H | Na⊕ | |
| 2.117 | NO$_2$ | H | i-C$_3$H$_7$ | H | H | H | Li⊕ | |
| 2.118 | NO$_2$ | H | i-C$_3$H$_7$ | H | H | H | ½Ca$^{2⊕}$ | |
| 2.119 | NO$_2$ | H | i-C$_3$H$_7$ | H | H | H | NH(CH$_3$)$_3$⊕ | |
| 2.120 | NO$_2$ | H | i-C$_3$H$_7$ | H | H | H | NH(C$_2$H$_5$OH)$_3$⊕ | |
| 2.121 | H | NO$_2$ | i-C$_3$H$_7$ | H | H | H | Na⊕ | |
| 2.122 | H | NO$_2$ | i-C$_3$H$_7$ | H | H | H | Li⊕ | |
| 2.123 | H | NO$_2$ | i-C$_3$H$_7$ | H | H | H | ½Ca$^{2⊕}$ | |
| 2.124 | H | NO$_2$ | i-C$_3$H$_7$ | H | H | H | NH(CH$_3$)$_3$⊕ | |
| 2.125 | H | NO$_2$ | i-C$_3$H$_7$ | H | H | H | NH(C$_2$H$_5$OH)$_3$⊕ | |
| 2.126 | H | H | i-C$_3$H$_7$ | H | H | H | Na⊕ | |
| 2.127 | H | H | i-C$_3$H$_7$ | H | H | H | Li⊕ | |
| 2.128 | H | H | i-C$_3$H$_7$ | H | H | H | ½Ca$^{2⊕}$ | |
| 2.129 | H | H | i-C$_3$H$_7$ | H | H | H | NH(CH$_3$)$_3$⊕ | |
| 2.130 | H | H | i-C$_3$H$_7$ | H | H | H | NH(C$_2$H$_5$OH)$_3$⊕ | |
| 2.131 | Cl | CCl$_3$ | i-C$_3$H$_7$ | H | H | H | Na⊕ | |
| 2.132 | Cl | CCl$_3$ | i-C$_3$H$_7$ | H | H | H | Li⊕ | |
| 2.133 | Cl | CCl$_3$ | i-C$_3$H$_7$ | H | H | H | ½Ca$^{2⊕}$ | |
| 2.134 | Cl | CCl$_3$ | i-C$_3$H$_7$ | H | H | H | NH(CH$_3$)$_3$⊕ | |
| 2.135 | Cl | CCl$_3$ | i-C$_3$H$_7$ | H | H | H | NH(C$_2$H$_5$OH)$_3$⊕ | |
| 2.136 | F | CF$_3$ | i-C$_3$H$_7$ | H | H | H | Na⊕ | |
| 2.137 | F | CF$_3$ | i-C$_3$H$_7$ | H | H | H | Li⊕ | |
| 2.138 | F | CF$_3$ | i-C$_3$H$_7$ | H | H | H | ½Ca$^{2⊕}$ | |
| 2.139 | F | CF$_3$ | i-C$_3$H$_7$ | H | H | H | NH(CH$_3$)$_3$⊕ | |
| 2.140 | F | CF$_3$ | i-C$_3$H$_7$ | H | H | H | NH(C$_2$H$_5$OH)$_3$⊕ | |
| 2.141 | Cl | Cl | C$_6$H$_5$ | H | H | H | Na⊕ | |
| 2.142 | Cl | Cl | C$_6$H$_5$ | H | H | H | Li⊕ | |
| 2.143 | Cl | Cl | C$_6$H$_5$ | H | H | H | ½Ca$^{2⊕}$ | |
| 2.144 | Cl | Cl | C$_6$H$_5$ | H | H | H | NH(CH$_3$)$_3$⊕ | |
| 2.145 | Cl | Cl | C$_6$H$_5$ | H | H | H | NH(C$_2$H$_5$OH)$_3$⊕ | |
| 2.146 | Cl | CF$_3$ | C$_6$H$_5$ | H | H | H | Na⊕ | |
| 2.147 | Cl | CF$_3$ | C$_6$H$_5$ | H | H | H | Li⊕ | |
| 2.148 | Cl | CF$_3$ | C$_6$H$_5$ | H | H | H | ½Ca$^{2⊕}$ | |
| 2.149 | Cl | CF$_3$ | C$_6$H$_5$ | H | H | H | NH(CH$_3$)$_3$⊕ | |
| 2.150 | Cl | CF$_3$ | C$_6$H$_5$ | H | H | H | NH(C$_2$H$_5$OH)$_3$⊕ | |
| 2.151 | NO$_2$ | H | C$_6$H$_5$ | H | H | H | Na⊕ | |
| 2.152 | NO$_2$ | H | C$_6$H$_5$ | H | H | H | Li⊕ | |
| 2.153 | NO$_2$ | H | C$_6$H$_5$ | H | H | H | ½Ca$^{2⊕}$ | |
| 2.154 | NO$_2$ | H | C$_6$H$_5$ | H | H | H | NH(CH$_3$)$_3$⊕ | |
| 2.155 | NO$_2$ | H | C$_6$H$_5$ | H | H | H | NH(C$_2$H$_5$OH)$_3$⊕ | |
| 2.156 | H | NO$_2$ | C$_6$H$_5$ | H | H | H | Na⊕ | |

TABLE 2-continued

Compounds of formula

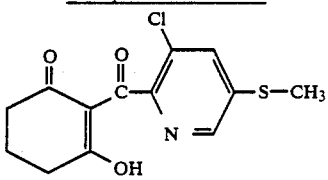

| Comp. No. | $R^1$ | $R^2$ | $R^3$ | $R^4$ | $R^5$ | $R^6$ | $M^\oplus$ | phys. data |
|---|---|---|---|---|---|---|---|---|
| 2.157 | H | $NO_2$ | $C_6H_5$ | H | H | H | $Li^\oplus$ | |
| 2.158 | H | $NO_2$ | $C_6H_5$ | H | H | H | $\frac{1}{2}Ca^{2\oplus}$ | |
| 2.159 | H | $NO_2$ | $C_6H_5$ | H | H | H | $NH(CH_3)_3^\oplus$ | |
| 2.160 | H | $NO_2$ | $C_6H_5$ | H | H | H | $NH(C_2H_5OH)_3^\oplus$ | |
| 2.161 | H | H | $C_6H_5$ | H | H | H | $Na^\oplus$ | |
| 2.162 | H | H | $C_6H_5$ | H | H | H | $Li^\oplus$ | |
| 2.163 | H | H | $C_6H_5$ | H | H | H | $\frac{1}{2}Ca^{2\oplus}$ | |
| 2.164 | H | H | $C_6H_5$ | H | H | H | $NH(CH_3)_3^\oplus$ | |
| 2.165 | H | H | $C_6H_5$ | H | H | H | $NH(C_2H_5OH)_3^\oplus$ | |
| 2.166 | Cl | $CCl_3$ | $C_6H_5$ | H | H | H | $Na^\oplus$ | |
| 2.167 | Cl | $CCl_3$ | $C_6H_5$ | H | H | H | $Li^\oplus$ | |
| 2.168 | Cl | $CCl_3$ | $C_6H_5$ | H | H | H | $\frac{1}{2}Ca^{2\oplus}$ | |
| 2.169 | Cl | $CCl_3$ | $C_6H_5$ | H | H | H | $NH(CH_3)_3^\oplus$ | |
| 2.170 | Cl | $CCl_3$ | $C_6H_5$ | H | H | H | $NH(C_2H_5OH)_3^\oplus$ | |
| 2.171 | F | $CF_3$ | $C_6H_5$ | H | H | H | $Na^\oplus$ | |
| 2.172 | F | $CF_3$ | $C_6H_5$ | H | H | H | $Li^\oplus$ | |
| 2.173 | F | $CF_3$ | $C_6H_5$ | H | H | H | $\frac{1}{2}Ca^{2\oplus}$ | |
| 2.174 | F | $CF_3$ | $C_6H_5$ | H | H | H | $NH(CH_3)_3^\oplus$ | |
| 2.175 | F | $CF_3$ | $C_6H_5$ | H | H | H | $NH(C_2H_5OH)_3^\oplus$ | |
| 2.176 | Cl | Cl | $CH_3$ | $CH_3$ | H | H | $Na^\oplus$ | |
| 2.177 | Cl | Cl | $CH_3$ | $CH_3$ | H | H | $Li^\oplus$ | |
| 2.178 | Cl | Cl | $CH_3$ | $CH_3$ | H | H | $\frac{1}{2}Ca^{2\oplus}$ | |
| 2.179 | Cl | Cl | $CH_3$ | $CH_3$ | H | H | $NH(CH_3)_3^\oplus$ | |
| 2.180 | Cl | Cl | $CH_3$ | $CH_3$ | H | H | $NH(C_2H_5OH)_3^\oplus$ | |
| 2.181 | Cl | $CF_3$ | $CH_3$ | $CH_3$ | H | H | $Na^\oplus$ | |
| 2.182 | Cl | $CF_3$ | $CH_3$ | $CH_3$ | H | H | $Li^\oplus$ | |
| 2.183 | Cl | $CF_3$ | $CH_3$ | $CH_3$ | H | H | $\frac{1}{2}Ca^{2\oplus}$ | |
| 2.184 | Cl | $CF_3$ | $CH_3$ | $CH_3$ | H | H | $NH(CH_3)_3^\oplus$ | |
| 2.185 | Cl | $CF_3$ | $CH_3$ | $CH_3$ | H | H | $NH(C_2H_5OH)_3^\oplus$ | |
| 2.186 | $NO_2$ | H | $CH_3$ | $CH_3$ | H | H | $Na^\oplus$ | |
| 2.187 | $NO_2$ | H | $CH_3$ | $CH_3$ | H | H | $Li^\oplus$ | |
| 2.188 | $NO_2$ | H | $CH_3$ | $CH_3$ | H | H | $\frac{1}{2}Ca^{2\oplus}$ | |
| 2.189 | $NO_2$ | H | $CH_3$ | $CH_3$ | H | H | $NH(CH_3)_3^\oplus$ | |
| 2.190 | $NO_2$ | H | $CH_3$ | $CH_3$ | H | H | $NH(C_2H_5OH)_3^\oplus$ | |
| 2.191 | H | $NO_2$ | $CH_3$ | $CH_3$ | H | H | $Na^\oplus$ | |
| 2.192 | H | $NO_2$ | $CH_3$ | $CH_3$ | H | H | $Li^\oplus$ | |
| 2.193 | H | $NO_2$ | $CH_3$ | $CH_3$ | H | H | $\frac{1}{2}Ca^{2\oplus}$ | |
| 2.194 | H | $NO_2$ | $CH_3$ | $CH_3$ | H | H | $NH(CH_3)_3^\oplus$ | |
| 2.195 | H | $NO_2$ | $CH_3$ | $CH_3$ | H | H | $NH(C_2H_5OH)_3^\oplus$ | |
| 2.196 | H | H | $CH_3$ | $CH_3$ | H | H | $Na^\oplus$ | |
| 2.197 | H | H | $CH_3$ | $CH_3$ | H | H | $Li^\oplus$ | |
| 2.198 | H | H | $CH_3$ | $CH_3$ | H | H | $\frac{1}{2}Ca^{2\oplus}$ | |
| 2.199 | H | H | $CH_3$ | $CH_3$ | H | H | $NH(CH_3)_3^\oplus$ | |
| 2.200 | H | H | $CH_3$ | $CH_3$ | H | H | $NH(C_2H_5OH)_3^\oplus$ | |
| 2.201 | Cl | $CCl_3$ | $CH_3$ | $CH_3$ | H | H | $Na^\oplus$ | |
| 2.202 | Cl | $CCl_3$ | $CH_3$ | $CH_3$ | H | H | $Li^\oplus$ | |
| 2.203 | Cl | $CCl_3$ | $CH_3$ | $CH_3$ | H | H | $\frac{1}{2}Ca^{2\oplus}$ | |
| 2.204 | Cl | $CCl_3$ | $CH_3$ | $CH_3$ | H | H | $NH(CH_3)_3^\oplus$ | |
| 2.205 | Cl | $CCl_3$ | $CH_3$ | $CH_3$ | H | H | $NH(C_2H_5OH)_3^\oplus$ | |
| 2.206 | F | $CF_3$ | $CH_3$ | $CH_3$ | H | H | $Na^\oplus$ | |
| 2.207 | F | $CF_3$ | $CH_3$ | $CH_3$ | H | H | $Li^\oplus$ | |
| 2.208 | F | $CF_3$ | $CH_3$ | $CH_3$ | H | H | $\frac{1}{2}Ca^{2\oplus}$ | |
| 2.209 | F | $CF_3$ | $CH_3$ | $CH_3$ | H | H | $NH(CH_3)_3^\oplus$ | |
| 2.210 | F | $CF_3$ | $CH_3$ | $CH_3$ | H | H | $NH(C_2H_5OH)_3^\oplus$ | |
| 2.211 | Cl | Cl | $CH_3$ | H | $CH_3$ | H | $Na^\oplus$ | |
| 2.212 | Cl | Cl | $CH_3$ | H | $CH_3$ | H | $Li^\oplus$ | |
| 2.213 | Cl | Cl | $CH_3$ | H | $CH_3$ | H | $\frac{1}{2}Ca^{2\oplus}$ | |
| 2.214 | Cl | Cl | $CH_3$ | H | $CH_3$ | H | $NH(CH_3)_3^\oplus$ | |
| 2.215 | Cl | Cl | $CH_3$ | H | $CH_3$ | H | $NH(C_2H_5OH)_3^\oplus$ | |
| 2.216 | Cl | $CF_3$ | $CH_3$ | H | $CH_3$ | H | $Na^\oplus$ | |
| 2.217 | Cl | $CF_3$ | $CH_3$ | H | $CH_3$ | H | $Li^\oplus$ | |
| 2.218 | Cl | $CF_3$ | $CH_3$ | H | $CH_3$ | H | $\frac{1}{2}Ca^{2\oplus}$ | |
| 2.219 | Cl | $CF_3$ | $CH_3$ | H | $CH_3$ | H | $NH(CH_3)_3^\oplus$ | |
| 2.220 | Cl | $CF_3$ | $CH_3$ | H | $CH_3$ | H | $NH(C_2H_5OH)_3^\oplus$ | |
| 2.221 | $NO_2$ | H | $CH_3$ | H | $CH_3$ | H | $Na^\oplus$ | |
| 2.222 | $NO_2$ | H | $CH_3$ | H | $CH_3$ | H | $Li^\oplus$ | |
| 2.223 | $NO_2$ | H | $CH_3$ | H | $CH_3$ | H | $\frac{1}{2}Ca^{2\oplus}$ | |
| 2.224 | $NO_2$ | H | $CH_3$ | H | $CH_3$ | H | $NH(CH_3)_3^\oplus$ | |
| 2.225 | $NO_2$ | H | $CH_3$ | H | $CH_3$ | H | $NH(C_2H_5OH)_3^\oplus$ | |
| 2.226 | H | $NO_2$ | $CH_3$ | H | $CH_3$ | H | $Na^\oplus$ | |

TABLE 2-continued

Compounds of formula

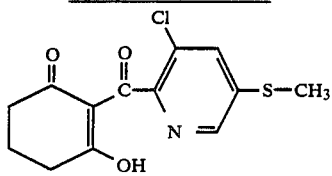

| Comp. No. | R¹ | R² | R³ | R⁴ | R⁵ | R⁶ | M⊕ | phys. data |
|---|---|---|---|---|---|---|---|---|
| 2.227 | H | NO₂ | CH₃ | H | CH₃ | H | Li⊕ | |
| 2.228 | H | NO₂ | CH₃ | H | CH₃ | H | ½Ca²⊕ | |
| 2.229 | H | NO₂ | CH₃ | H | CH₃ | H | NH(CH₃)₃⊕ | |
| 2.230 | H | NO₂ | CH₃ | H | CH₃ | H | NH(C₂H₅OH)₃⊕ | |
| 2.231 | H | H | CH₃ | H | CH₃ | H | Na⊕ | |
| 2.232 | H | H | CH₃ | H | CH₃ | H | Li⊕ | |
| 2.233 | H | H | CH₃ | H | CH₃ | H | ½Ca²⊕ | |
| 2.234 | H | H | CH₃ | H | CH₃ | H | NH(CH₃)₃⊕ | |
| 2.235 | H | H | CH₃ | H | CH₃ | H | NH(C₂H₅OH)₃⊕ | |
| 2.236 | Cl | CCl₃ | CH₃ | H | CH₃ | H | Na⊕ | |
| 2.237 | Cl | CCl₃ | CH₃ | H | CH₃ | H | Li⊕ | |
| 2.238 | Cl | CCl₃ | CH₃ | H | CH₃ | H | ½Ca²⊕ | |
| 2.239 | Cl | CCl₃ | CH₃ | H | CH₃ | H | NH(CH₃)₃⊕ | |
| 2.240 | Cl | CCl₃ | CH₃ | H | CH₃ | H | NH(C₂H₅OH)₃⊕ | |
| 2.241 | F | CF₃ | CH₃ | H | CH₃ | H | Na⊕ | |
| 2.242 | F | CF₃ | CH₃ | H | CH₃ | H | Li⊕ | |
| 2.243 | F | CF₃ | CH₃ | H | CH₃ | H | ½Ca²⊕ | |
| 2.244 | F | CF₃ | CH₃ | H | CH₃ | H | NH(CH₃)₃⊕ | |
| 2.245 | F | CF₃ | CH₃ | H | CH₃ | H | NH(C₂H₅OH)₃⊕ | |
| 2.246 | Cl | Cl | H | H | H | CN | Na⊕ | |
| 2.247 | Cl | Cl | H | H | H | CN | Li⊕ | |
| 2.248 | Cl | Cl | H | H | H | CN | ½Ca²⊕ | |
| 2.249 | Cl | Cl | H | H | H | CN | NH(CH₃)₃⊕ | |
| 2.250 | Cl | Cl | H | H | H | CN | NH(C₂H₅OH)₃⊕ | |
| 2.251 | Cl | CF₃ | H | H | H | CN | Na⊕ | |
| 2.252 | Cl | CF₃ | H | H | H | CN | Li⊕ | |
| 2.253 | Cl | CF₃ | H | H | H | CN | ½Ca²⊕ | |
| 2.254 | Cl | CF₃ | H | H | H | CN | NH(CH₃)₃⊕ | |
| 2.255 | Cl | CF₃ | H | H | H | CN | NH(C₂H₅OH)₃⊕ | |
| 2.256 | NO₂ | H | H | H | H | CN | Na⊕ | |
| 2.257 | NO₂ | H | H | H | H | CN | Li⊕ | |
| 2.258 | NO₂ | H | H | H | H | CN | ½Ca²⊕ | |
| 2.259 | NO₂ | H | H | H | H | CN | NH(CH₃)₃⊕ | |
| 2.260 | NO₂ | H | H | H | H | CN | NH(C₂H₅OH)₃⊕ | |
| 2.261 | H | NO₂ | H | H | H | CN | Na⊕ | |
| 2.262 | H | NO₂ | H | H | H | CN | Li⊕ | |
| 2.263 | H | NO₂ | H | H | H | CN | ½Ca²⊕ | |
| 2.264 | H | NO₂ | H | H | H | CN | NH(CH₃)₃⊕ | |
| 2.265 | H | NO₂ | H | H | H | CN | NH(C₂H₅OH)₃⊕ | |
| 2.266 | H | H | H | H | H | CN | Na⊕ | |
| 2.267 | H | H | H | H | H | CN | Li⊕ | |
| 2.268 | H | H | H | H | H | CN | ½Ca²⊕ | |
| 2.269 | H | H | H | H | H | CN | NH(CH₃)₃⊕ | |
| 2.270 | H | H | H | H | H | CN | NH(C₂H₅OH)₃⊕ | |
| 2.271 | Cl | CCl₃ | H | H | H | CN | Na⊕ | |
| 2.272 | Cl | CCl₃ | H | H | H | CN | Li⊕ | |
| 2.273 | Cl | CCl₃ | H | H | H | CN | ½Ca²⊕ | |
| 2.274 | Cl | CCl₃ | H | H | H | CN | NH(CH₃)₃⊕ | |
| 2.275 | Cl | CCl₃ | H | H | H | CN | NH(C₂H₅OH)₃⊕ | |
| 2.276 | F | CF₃ | H | H | H | CN | Na⊕ | |
| 2.277 | F | CF₃ | H | H | H | CN | Li⊕ | |
| 2.278 | F | CF₃ | H | H | H | CN | ½Ca²⊕ | |
| 2.279 | F | CF₃ | H | H | H | CN | NH(CH₃)₃⊕ | |
| 2.280 | F | CF₃ | H | H | H | CN | NH(C₂H₅OH)₃⊕ | |
| 2.281 | Cl | Cl | H | H | H | CN | Na⊕ | |
| 2.282 | Cl | Cl | H | H | H | CN | Li⊕ | |
| 2.283 | Cl | Cl | H | H | H | CN | ½Ca²⊕ | |
| 2.284 | Cl | Cl | H | H | H | CN | NH(CH₃)₃⊕ | |
| 2.285 | Cl | Cl | H | H | H | CN | NH(C₂H₅OH)₃⊕ | |
| 2.286 | Cl | CF₃ | H | H | H | CN | Na⊕ | |
| 2.287 | Cl | CF₃ | H | H | H | CN | Li⊕ | |
| 2.288 | Cl | CF₃ | H | H | H | CN | ½Ca²⊕ | |
| 2.289 | Cl | CF₃ | H | H | H | CN | NH(CH₃)₃⊕ | |
| 2.290 | Cl | CF₃ | H | H | H | CN | NH(C₂H₅OH)₃⊕ | |
| 2.291 | NO₂ | H | CH₃ | H | H | CN | Na⊕ | |
| 2.292 | NO₂ | H | CH₃ | H | H | CN | Li⊕ | |
| 2.293 | NO₂ | H | CH₃ | H | H | CN | ½Ca²⊕ | |
| 2.294 | NO₂ | H | CH₃ | H | H | CN | NH(CH₃)₃⊕ | |
| 2.295 | NO₂ | H | CH₃ | H | H | CN | NH(C₂H₅OH)₃⊕ | |
| 2.296 | H | NO₂ | CH₃ | H | H | CN | Na⊕ | |

TABLE 2-continued

Compounds of formula

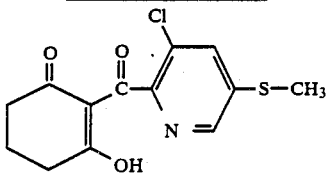

| Comp. No. | R¹ | R² | R³ | R⁴ | R⁵ | R⁶ | M⊕ | phys. data |
|---|---|---|---|---|---|---|---|---|
| 2.297 | H | NO₂ | CH₃ | H | H | CN | Li⊕ | |
| 2.298 | H | NO₂ | CH₃ | H | H | CN | ½Ca²⊕ | |
| 2.299 | H | NO₂ | CH₃ | H | H | CN | NH(CH₃)₃⊕ | |
| 2.300 | H | NO₂ | CH₃ | H | H | CN | NH(C₂H₅OH)₃⊕ | |
| 2.301 | H | H | CH₃ | H | H | CN | Na⊕ | |
| 2.302 | H | H | CH₃ | H | H | CN | Li⊕ | |
| 2.303 | H | H | CH₃ | H | H | CN | ½Ca²⊕ | |
| 2.304 | H | H | CH₃ | H | H | CN | NH(CH₃)₃⊕ | |
| 2.305 | H | H | CH₃ | H | H | CN | NH(C₂H₅OH)₃⊕ | |
| 2.306 | Cl | CCl₃ | CH₃ | H | H | CN | Na⊕ | |
| 2.307 | Cl | CCl₃ | CH₃ | H | H | CN | Li⊕ | |
| 2.308 | Cl | CCl₃ | CH₃ | H | H | CN | ½Ca²⊕ | |
| 2.309 | Cl | CCl₃ | CH₃ | H | H | CN | NH(CH₃)₃⊕ | |
| 2.310 | Cl | CCl₃ | CH₃ | H | H | CN | NH(C₂H₅OH)₃⊕ | |
| 2.311 | F | CF₃ | CH₃ | H | H | CN | Na⊕ | |
| 2.312 | F | CF₃ | CH₃ | H | H | CN | Li⊕ | |
| 2.313 | F | CF₃ | CH₃ | H | H | CN | ½Ca²⊕ | |
| 2.314 | F | CF₃ | CH₃ | H | H | CN | NH(CH₃)₃⊕ | |
| 2.315 | F | CF₃ | CH₃ | H | H | CN | NH(C₂H₅OH)₃⊕ | |
| 2.316 | Cl | Cl | C₆H₅—CH₂— | H | H | H | Na⊕ | |
| 2.317 | Cl | Cl | C₆H₅—CH₂— | H | H | H | Li⊕ | |
| 2.318 | Cl | Cl | C₆H₅—CH₂— | H | H | H | ½Ca²⊕ | |
| 2.319 | Cl | Cl | C₆H₅—CH₂— | H | H | H | NH(CH₃)₃⊕ | |
| 2.320 | Cl | Cl | C₆H₅—CH₂— | H | H | H | NH(C₂H₅OH)₃⊕ | |
| 2.321 | Cl | CF₃ | C₆H₅—CH₂— | H | H | H | Na⊕ | |
| 2.322 | Cl | CF₃ | C₆H₅—CH₂— | H | H | H | Li⊕ | |
| 2.323 | Cl | CF₃ | C₆H₅—CH₂— | H | H | H | ½Ca²⊕ | |
| 2.324 | Cl | CF₃ | C₆H₅—CH₂— | H | H | H | NH(CH₃)₃⊕ | |
| 2.325 | Cl | CF₃ | C₆H₅—CH₂— | H | H | H | NH(C₂H₅OH)₃⊕ | |
| 2.326 | NO₂ | H | C₆H₅—CH₂— | H | H | H | Na⊕ | |
| 2.327 | NO₂ | H | C₆H₅—CH₂— | H | H | H | Li⊕ | |
| 2.328 | NO₂ | H | C₆H₅—CH₂— | H | H | H | ½Ca²⊕ | |
| 2.329 | NO₂ | H | C₆H₅—CH₂— | H | H | H | NH(CH₃)₃⊕ | |
| 2.330 | NO₂ | H | C₆H₅—CH₂— | H | H | H | NH(C₂H₅OH)₃⊕ | |
| 2.331 | H | NO₂ | C₆H₅—CH₂— | H | H | H | Na⊕ | |
| 2.332 | H | NO₂ | C₆H₅—CH₂— | H | H | H | Li⊕ | |
| 2.333 | H | NO₂ | C₆H₅—CH₂— | H | H | H | ½Ca²⊕ | |
| 2.334 | H | NO₂ | C₆H₅—CH₂— | H | H | H | NH(CH₃)₃⊕ | |
| 2.335 | H | NO₂ | C₆H₅—CH₂— | H | H | H | NH(C₂H₅OH)₃⊕ | |
| 2.336 | H | H | C₆H₅—CH₂— | H | H | H | Na⊕ | |
| 2.337 | H | H | C₆H₅—CH₂— | H | H | H | Li⊕ | |
| 2.338 | H | H | C₆H₅—CH₂— | H | H | H | ½Ca²⊕ | |
| 2.339 | H | H | C₆H₅—CH₂— | H | H | H | NH(CH₃)₃⊕ | |
| 2.340 | H | H | C₆H₅—CH₂— | H | H | H | NH(C₂H₅OH)₃⊕ | |
| 2.341 | Cl | CCl₃ | C₆H₅—CH₂— | H | H | H | Na⊕ | |
| 2.342 | Cl | CCl₃ | C₆H₅—CH₂— | H | H | H | Li⊕ | |
| 2.343 | Cl | CCl₃ | C₆H₅—CH₂— | H | H | H | ½Ca²⊕ | |
| 2.344 | Cl | CCl₃ | C₆H₅—CH₂— | H | H | H | NH(CH₃)₃⊕ | |
| 2.345 | Cl | CCl₃ | C₆H₅—CH₂— | H | H | H | NH(C₂H₅OH)₃⊕ | |
| 2.346 | F | CF₃ | C₆H₅—CH₂— | H | H | H | Na⊕ | |
| 2.347 | F | CF₃ | C₆H₅—CH₂ | H | H | H | Li⊕ | |
| 2.348 | F | CF₃ | C₆H₅—CH₂— | H | H | H | ½Ca²⊕ | |
| 2.349 | F | CF₃ | C₆H₅—CH₂— | H | H | H | NH(CH₃)₃⊕ | |
| 2.350 | F | CF₃ | C₆H₅—CH₂— | H | H | H | NH(C₂H₅OH)₃⊕ | |
| 2.351 | Cl | Cl | C₆H₅ | H | H | COOCH₃ | Na⊕ | |
| 2.352 | Cl | Cl | C₆H₅ | H | H | COOCH₃ | Li⊕ | |
| 2.353 | Cl | Cl | C₆H₅ | H | H | COOCH₃ | ½Ca²⊕ | |
| 2.354 | Cl | Cl | C₆H₅ | H | H | COOCH₃ | NH(CH₃)₃⊕ | |
| 2.355 | Cl | Cl | C₆H₅ | H | H | COOCH₃ | NH(C₂H₅OH)₃⊕ | |
| 2.356 | Cl | CF₃ | C₆H₅ | H | H | COOCH₃ | Na⊕ | |
| 2.357 | Cl | CF₃ | C₆H₅ | H | H | COOCH₃ | Li⊕ | |
| 2.358 | Cl | CF₃ | C₆H₅ | H | H | COOCH₃ | ½Ca²⊕ | |
| 2.359 | Cl | CF₃ | C₆H₅ | H | H | COOCH₃ | NH(CH₃)₃⊕ | |
| 2.360 | Cl | CF₃ | C₆H₅ | H | H | COOCH₃ | NH(C₂H₅OH)₃⊕ | |
| 2.361 | NO₂ | H | C₆H₅ | H | H | COOCH₃ | Na⊕ | |
| 2.362 | NO₂ | H | C₆H₅ | H | H | COOCH₃ | Li⊕ | |
| 2.363 | NO₂ | H | C₆H₅ | H | H | COOCH₃ | ½Ca²⊕ | |
| 2.364 | NO₂ | H | C₆H₅ | H | H | COOCH₃ | NH(CH₃)₃⊕ | |
| 2.365 | NO₂ | H | C₆H₅ | H | H | COOCH₃ | NH(C₂H₅OH)₃⊕ | |
| 2.366 | H | NO₂ | C₆H₅ | H | H | COOCH₃ | Na⊕ | |

TABLE 2-continued

Compounds of formula

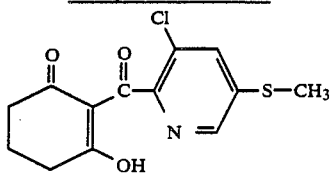

| Comp. No. | R¹ | R² | R³ | R⁴ | R⁵ | R⁶ | M⊕ | phys. data |
|---|---|---|---|---|---|---|---|---|
| 2.367 | H | NO₂ | C₆H₅ | H | H | COOCH₃ | Li⊕ | |
| 2.368 | H | NO₂ | C₆H₅ | H | H | COOCH₃ | ½Ca²⊕ | |
| 2.369 | H | NO₂ | C₆H₅ | H | H | COOCH₃ | NH(CH₃)₃⊕ | |
| 2.370 | H | NO₂ | C₆H₅ | H | H | COOCH₃ | NH(C₂H₅OH)₃⊕ | |
| 2.371 | H | H | C₆H₅ | H | H | COOCH₃ | Na⊕ | |
| 2.372 | H | H | C₆H₅ | H | H | COOCH₃ | Li⊕ | |
| 2.373 | H | H | C₆H₅ | H | H | COOCH₃ | ½Ca²⊕ | |
| 2.374 | H | H | C₆H₅ | H | H | COOCH₃ | NH(CH₃)₃⊕ | |
| 2.375 | H | H | C₆H₅ | H | H | COOCH₃ | NH(C₂H₅OH)₃⊕ | |
| 2.376 | Cl | CCl₃ | C₆H₅ | H | H | COOCH₃ | Na⊕ | |
| 2.377 | Cl | CCl₃ | C₆H₅ | H | H | COOCH₃ | Li⊕ | |
| 2.378 | Cl | CCl₃ | C₆H₅ | H | H | COOCH₃ | ½Ca²⊕ | |
| 2.379 | Cl | CCl₃ | C₆H₅ | H | H | COOCH₃ | NH(CH₃)₃⊕ | |
| 2.380 | Cl | CCl₃ | C₆H₅ | H | H | COOCH₃ | NH(C₂H₅OH)₃⊕ | |
| 2.381 | F | CF₃ | C₆H₅ | H | H | COOCH₃ | Na⊕ | |
| 2.382 | F | CF₃ | C₆H₅ | H | H | COOCH₃ | Li⊕ | |
| 2.383 | F | CF₃ | C₆H₅ | H | H | COOCH₃ | ½Ca²⊕ | |
| 2.384 | F | CF₃ | C₆H₅ | H | H | COOCH₃ | NH(CH₃)₃⊕ | |
| 2.385 | F | CF₃ | C₆H₅ | H | H | COOCH₃ | NH(C₂H₅OH)₃⊕ | |

P.2.1. Preparation of the pyridinecarboxylic acid halides of formula II

P.2.1.1. Preparation of 5-trifluoromethylpyridine-2-carboxylic acid chloride 9.8 ml (0.11 mol) of oxalyl chloride are added dropwise to a suspension of 22.9 g (0.1 mol) of the potassium salt of 5-trifluoromethylpyridine2-carboxylic acid and 10 drops of DMF in 250 ml of toluene, the temperature rising to 40° C. and brisk evolution of gas occurring. The whole is then stirred for 2 hours at 40° C. The light-brown suspension is subsequently concentrated by evaporation on a rotary evaporator, stirred with 250 ml of absolute ether, filtered and concentrated by evaporation again.

17.8 g (85%) of the title compound of formula

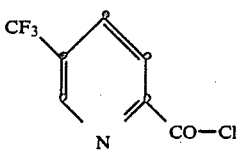

are isolated in the form of a brown oil (Compound No. 3.078).

P.2.1.2. Preparation of 3-chloro-5-trifluoromethyl-pyridine-2-carboxylic acid ethyl ester 216 g (1 mol) of 2,3-dichloro-5-trifluoromethylpyridine, 16.7 g of [PdCl₂(PPh₃)₂] and 420 ml (3 mol) of triethylamine are stirred for 14 hours at 50 bar and 100° C. in 3.3 l of ethanol in a CO atmosphere. The whole is then concentrated by evaporation on a rotary evaporator at 40° C. The resulting mass is stirred with 2 l of ether, the triethylamine hydrochloride is filtered off, and the filtrate is concentrated by evaporation on a rotary evaporator. 245 g of a brown oil are obtained, which is purified on silica gel with ethyl acetate/hexane (1:9).

206.8 g (81.6%) of the title compound of formula

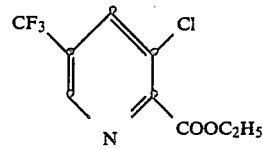

are isolated in the form of a yellow oil (Compound No. 3.005).

P.2.1.3. Preparation of 3-chloro-5-trifluoromethyl-pyridine-2-carboxylic acid 76 g (0.3 mol) of 3-chloro-5-trifluoromethylpyridine-2-carboxylic acid ethyl ester are stirred for 6 hours with 165 ml (0.33 mol) of 2N NaOH. The resulting solution is washed twice with methylene chloride. The aqueous solution is then adjusted to pH 1 with 37% hydrochloric acid and the product is filtered off with suction and dried at room temperature in vacuo.

65 g (96%) of the title compound of formula

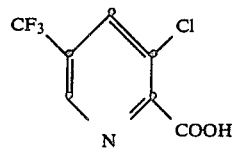

are isolated in the form of white crystals having a melting point of 135° C. (decomp.) (Compound No. 3.039).

P.2.1.4. Preparation of 3-chloro-5-trifluoromethyl-pyridine-2-carboxylic acid chloride 16.9 g (75 mmol) of 3-chloro-5-trifluoromethylpyridine-2-carboxylic acid are suspended in 75 ml of hexane. After the addition of 2 drops of DMF 7 ml (80 mmol) of oxalyl chloride in 25 ml of hexane are added dropwise. The whole is then stirred for 4 hours at 50° C. until the evolution of gas has ceased. The reaction solution is filtered and concentrated by evaporation on a rotary evaporator.

18 g (98%) of the title compound of formula

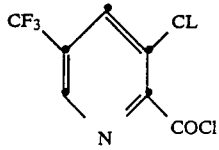

are isolated in the form of a yellow oil (Compound No. 3.073).

The compounds of Table 3 can be synthesised analogously to the above preparation processes.

P.2.1.5. Preparation of 3,5-dichloropyridine-2-carboxylic acid ethyl ester 250 g (1.3 mol) of 95% 2,3,5-trichloropyridine are reacted and purified as described in P.2.1.2.

147 g (51.5%) of the title compound of formula

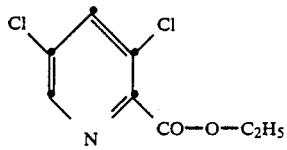

P.2.1.6. Preparation of 3-chloro-5-methylthio-2-carboxylic acid ethyl ester 8.6 g (0.18 mol) of methylmercaptan are introduced into a suspension of 17.9 g (0.16 mol) of potassium tert.-butoxide and 4.8 g of polyethylene glycol 1500 in 480 ml of toluene at from 25° to 30° C. The whole is then stirred for 15 minutes at 35° C. The resulting white suspension is cooled to −30° C. and 35.2 g (0.16 mol) of 3,5-dichloropyridine-2-carboxylic acid ethyl ester are added, the whole is warmed to from 20° to 25° C. and stirred at that temperature for 15 hours. The potassium chloride is filtered off from the reaction mixture and the filtrate is concentrated by evaporation on a rotary evaporator. 41 g of a yellow oil are obtained, which is purified on silica gel with petroleum ether/ether (3:1).

16 g (43.3% of the title compound of formula

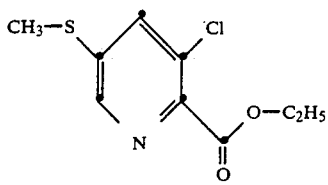

are isolated in the form of a yellow oil (Compound No. 3.018).

P.2.1.7. Preparation of 3-chloro-5-methylthiopyridine-2-carboxylic acid 22 g (0.095 mol) of 3-chloro-5-methylthiopyridine-2-carboxylic acid ethyl ester are reacted and purified analogously to P.2.1.3..

18.3 g (94.7%) of the title compound of formula

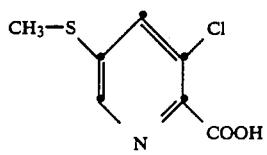

are isolated in the form of white crystals (Compound No. 3.052).

P.2.1.8. Preparation of 3-chloro-5-methylthiopyridine-2-carboxylic acid chloride 9.8 g (0.048 mol) of 3-chloro-5-methylthiopyridine-2-carboxylic acid are suspended in 65 ml of hexane and 25 ml of dichloroethane. After the addition of 2 drops of DMF and heating to 55° C., 4.9 ml (0.055 mol) of oxalyl chloride are added dropwise. The whole is then stirred for 4 hours at 55° C., until the evolution of gas has ceased. The reaction solution is filtered and concentrated by evaporation on a rotary evaporator.

10.6 g (99.5%) of the title compound of formula

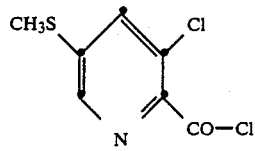

are isolated in the form of yellow, wax-like crystals (Compound No. 3.086).

P.2.2.1. 3-Chloro-5-methylsulfonyl-pyridin-2-carboxylic acid ethylester 44 g (140 mmol) 55% 3-chloroperbenzoic acid in 150 ml dichloromethane are added to a solution of 16.2 g (70 mmol) of 3-chlor-5-methylthiopyridin-2-carboxylic acid ethylester in such a manner that the temperature does not exced 30° C. The mixture is then stirred for 15 hours at room temperature and again 19 g (70 mmol) 3-chloroperbenzoic acid in 75 ml dichloromethane are added to this suspension to complete reaction. It is then stirred for another 3 hours at room temperature. The white suspension is diluted with 200 ml dichloromethane and filtered off from the 3-dichlorobenzoic acid. The filtrate is washed with 5% NaHCO3 solution and water and concentrated by evaporation on a rotary evaporator.

15.3 g (83%) of the title compound of formula

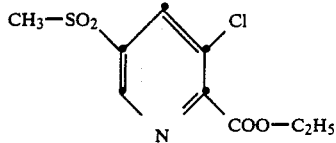

are isolated in the form of crystals of a m.p. of 90°-93° C. (Compound No. 3.017).

P.2.2.2. 3-Chloro-5-methylsulfonyl-pyridine-2-carboxylic acid 13.2 g (0.05 mol) 3-chloro-5-methylsulfonyl-pyridine-2-carboxylic acid ethylester are added to a mixture of 55 ml (0.055 mol) 1N NaOH and 5.5 ml ethanol. The temperature rises to 32° C. It is stirred for 3 hours at room temperature. This solution is then diluted with 150 ml of water, washed twice with dichloromethane and is then adjusted at a low pH by adding 37% HCl. The product is filtered off, washed with ice water and dried.

10.4 g (88.3%) of the title compound of formula

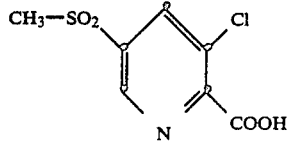

are isolated in the form of crystals with a m.p. of >150° C. (decomp.) (Compound No. 3.051).

P.2.2.3. 3-Chloro-5-methylsulfonyl-pyridin-2-carboxylic acid chloride 9.9 g (0.042 mol) of 3-chloro-5-methanesulfonyl-pyridine-2-carboxylic acid in 100 ml toluene and 4.4 ml (0.06 mol) thionylchloride are heated up to the boiling point for 2 hours. The brown suspension is then concentrated by evaporation on a rotary evaporator.

10.4 g (97.5%) of the title compound of formula

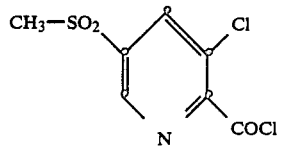

are isolated in the form of a brown wax (Compound No. 3.086).

TABLE 3

Compounds of formula

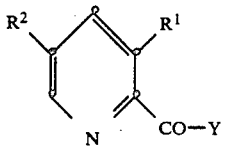

| Comp. No. | $R^1$ | $R^2$ | Y | phys. data |
|---|---|---|---|---|
| 3.001 | Cl | Cl | $OC_2H_5$ | oil |
| 3.002 | Cl | H | $OC_2H_5$ | oil |
| 3.003 | H | Cl | $OC_2H_5$ | m.p. 56–58° C. |
| 3.004 | H | H | $OC_2H_5$ | |
| 3.005 | Cl | $CF_3$ | $OC_2H_5$ | oil |
| 3.006 | $NO_2$ | H | $OC_2H_5$ | |
| 3.007 | H | $NO_2$ | $OC_2H_5$ | m.p. 89–91° C. |
| 3.008 | $NO_2$ | Cl | $OC_2H_5$ | |
| 3.009 | $CF_3$ | H | $OC_2H_5$ | |
| 3.010 | H | $CF_3$ | $OC_2H_5$ | m.p. 43–45° C. |
| 3.011 | $OCH_3$ | H | $OC_2H_5$ | |
| 3.012 | CN | H | $OC_2H_5$ | |
| 3.013 | $OCH_3$ | Cl | $OC_2H_5$ | |
| 3.014 | CN | Cl | $OC_2H_5$ | |
| 3.015 | Br | Cl | $OC_2H_5$ | |
| 3.016 | $SCH_3$ | Cl | $OC_2H_5$ | m.p. 77–80° C. |
| 3.017 | $SO_2CH_3$ | Cl | $OC_2H_5$ | m.p. 90–93° C. |
| 3.018 | Cl | $SCH_3$ | $OC_2H_5$ | oil |
| 3.019 | Cl | $SOCH_3$ | $OC_2H_5$ | |
| 3.020 | Cl | $SO_2CH_3$ | $OC_2H_5$ | |
| 3.021 | $SOCH_3$ | Cl | $OC_2H_5$ | |
| 3.022 | $SO_2CH_3$ | H | $OC_2H_5$ | |
| 3.023 | H | $SO_2CH_3$ | $OC_2H_5$ | |
| 3.024 | H | $CH_3$ | $OC_2H_5$ | oil |
| 3.025 | Cl | F | $OC_2H_5$ | oil |
| 3.026 | H | $CF_3$ | $OC_2H_5$ | |
| 3.027 | F | F | $OC_2H_5$ | |
| 3.028 | F | $CF_3$ | $OC_2H_5$ | |
| 3.029 | $CF_3$ | F | $OC_2H_5$ | |
| 3.030 | H | $CCl_3$ | $OC_2H_5$ | |
| 3.031 | $CCl_3$ | H | $OC_2H_5$ | |

TABLE 3-continued

Compounds of formula

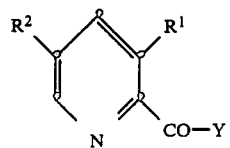

| Comp. No. | $R^1$ | $R^2$ | Y | phys. data |
|---|---|---|---|---|
| 3.032 | Cl | $CCl_3$ | $OC_2H_5$ | |
| 3.033 | $CCl_3$ | Cl | $OC_2H_5$ | |
| 3.034 | $CH_3$ | H | $OC_2H_5$ | |
| 3.035 | Cl | Cl | OH | m.p. 157° C. (decomp.) |
| 3.036 | Cl | H | OH | m.p. >125° C. (decomp.) |
| 3.037 | H | Cl | OH | m.p. 135° C. (decomp.) |
| 3.038 | H | H | OH | |
| 3.039 | Cl | $CF_3$ | OH | m.p. 135° C. (decomp.) |
| 3.040 | $NO_2$ | H | OH | |
| 3.041 | H | $NO_2$ | OH | |
| 3.042 | $NO_2$ | Cl | OH | |
| 3.043 | $CF_3$ | H | OH | m.p. 129–131° C. |
| 3.044 | H | $CF_3$ | OH | |
| 3.045 | $OCH_3$ | H | OH | |
| 3.046 | CN | H | OH | |
| 3.047 | $OCH_3$ | Cl | OH | |
| 3.048 | CN | Cl | OH | |
| 3.049 | Br | Cl | OH | |
| 3.050 | $SCH_3$ | Cl | OH | |
| 3.051 | $SO_2CH_3$ | Cl | OH | m.p. >150° C. (decomp.) |
| 3.052 | Cl | $SCH_3$ | OH | solid |
| 3.053 | Cl | $SOCH_3$ | OH | |
| 3.054 | Cl | $SO_2CH_3$ | OH | |
| 3.055 | $SOCH_3$ | Cl | OH | |
| 3.056 | $SO_2CH_3$ | H | OH | |
| 3.057 | H | $SO_2CH_3$ | OH | |
| 3.058 | H | $CH_3$ | OH | m.p. >135° C. (decomp.) |
| 3.059 | Cl | F | OH | m.p. >143° C. (decomp.) |
| 3.060 | H | $CF_3$ | OH | |
| 3.061 | F | F | OH | |
| 3.062 | F | $CF_3$ | OH | |
| 3.063 | $CF_3$ | F | OH | |
| 3.064 | H | $CCl_3$ | OH | |
| 3.065 | $CCl_3$ | H | OH | |
| 3.066 | Cl | $CCl_3$ | OH | |
| 3.067 | $CCl_3$ | Cl | OH | |
| 3.068 | $CH_3$ | H | OH | |
| 3.069 | Cl | Cl | Cl | m.p. 54–56° C. |
| 3.070 | Cl | H | Cl | solid |
| 3.071 | H | Cl | Cl | solid |
| 3.072 | H | H | Cl | |
| 3.073 | Cl | $CF_3$ | Cl | oil |
| 3.074 | $NO_2$ | H | Cl | |
| 3.075 | H | $NO_2$ | Cl | |
| 3.076 | $NO_2$ | Cl | Cl | |
| 3.077 | $CF_3$ | H | Cl | oil |
| 3.078 | H | $CF_3$ | Cl | oil |
| 3.079 | $OCH_3$ | H | Cl | |
| 3.080 | CN | H | Cl | |
| 3.081 | $OCH_3$ | Cl | Cl | |
| 3.082 | CN | Cl | Cl | |
| 3.083 | Br | Cl | Cl | |
| 3.084 | $SCH_3$ | Cl | Cl | |
| 3.085 | $SO_2CH_3$ | Cl | Cl | |
| 3.086 | Cl | $SCH_3$ | Cl | solid |
| 3.087 | Cl | $SOCH_3$ | Cl | |
| 3.088 | Cl | $SO_2CH_3$ | Cl | |
| 3.089 | $SOCH_3$ | Cl | Cl | |
| 3.090 | $SO_2CH_3$ | H | Cl | |
| 3.091 | H | $SO_2CH_3$ | Cl | |
| 3.092 | H | $CH_3$ | Cl | oil |
| 3.093 | Cl | F | Cl | oil |
| 3.094 | H | $CF_3$ | Cl | |

TABLE 3-continued

Compounds of formula

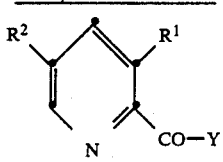

| Comp. No. | R¹ | R² | Y | phys. data |
|---|---|---|---|---|
| 3.095 | F | F | Cl | |
| 3.096 | F | CF₃ | Cl | |
| 3.097 | CF₃ | F | Cl | |
| 3.098 | H | CCl₃ | Cl | |
| 3.099 | CCl₃ | H | Cl | |
| 3.100 | Cl | CCl₃ | Cl | |
| 3.101 | CCl₃ | Cl | Cl | |
| 3.102 | CH₃ | H | Cl | |
| 3.103 | Cl | OCH₃ | OC₂H₅ | |
| 3.104 | Cl | OCH₃ | OH | solid |
| 3.105 | Cl | OCH₃ | Cl | solid |
| 3.106 | H | OCH₃ | OC₂H₅ | |
| 3.107 | H | OCH₃ | OH | |
| 3.108 | H | OCH₃ | Cl | |
| 3.109 | H | OC₃H₇(i) | OC₂H₅ | |
| 3.110 | H | OC₃H₇(i) | OH | |
| 3.111 | H | OC₃H₇(i) | Cl | |
| 3.112 | H | OCH₃ | OCH₃ | m.p. 27–74° C. |
| 3.113 | H | SCH₃ | OC₂H₅ | m.p. 46–48° C. |
| 3.114 | H | SCH₃ | OH | m.p. 159–160° C. |
| 3.115 | H | SCH₃ | Cl | solid |
| 3.116 | Cl | SC₂H₅ | OH | |
| 3.117 | Cl | SC₂H₅ | OC₂H₅ | |
| 3.118 | Cl | SC₂H₅ | Cl | |
| 3.119 | Cl | SOC₂H₅ | OH | |
| 3.120 | Cl | SOC₂H₅ | OC₂H₅ | |
| 3.121 | Cl | SOC₂H₅ | Cl | |
| 3.122 | Cl | SO₂C₃H₇(i) | OH | |
| 3.123 | Cl | SOC₃H₇(i) | OH | |
| 3.124 | Cl | SC₃H₇(i) | OH | |
| 3.125 | Cl | SO₂C₃H₇(i) | OC₂H₅ | |
| 3.126 | Cl | SOC₃H₇(i) | OC₂H₅ | |
| 3.127 | Cl | SC₃H₇(i) | OC₂H₅ | |
| 3.128 | Cl | SO₂C₃H₇(i) | Cl | |
| 3.129 | Cl | SOC₃H₇(i) | Cl | |
| 3.130 | Cl | SC₃H₇(i) | Cl | |
| 3.131 | Cl | OC₃H₇(i) | OH | |
| 3.132 | Cl | OC₃H₇(i) | OC₂H₅ | |
| 3.133 | Cl | OC₃H₇(i) | Cl | |
| 3.134 | SCH₃ | SCH₃ | OC₂H₅ | m.p. 60–70° C. |
| 3.135 | Cl | Br | OH | |
| 3.136 | Cl | Br | OC₂H₅ | |
| 3.137 | Cl | Br | Cl | |
| 3.138 | Cl | OCH₃ | OCH₃ | m.p. 72–74° C. |
| 3.139 | Cl | Cl | COOC₂H₅ | oil |

F. FORMULATION EXAMPLES

Example F1

Formulation Examples for active ingredients of formula I (throughout, percentages are by weight)

| (a) Emulsifiable concentrates | (a) | (b) | (c) |
|---|---|---|---|
| a compound according to Table 1 or 2 | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any desired concentration can be produced from such concentrates by dilution with water.

| (b) Solutions | (a) | (b) | (c) |
|---|---|---|---|
| a compound according Table 1 or 2 | 80% | 10% | 5% |
| ethylene glycol monomethyl ether | 20% | — | — |
| polyethylene glycol MW 400 | — | 70% | — |
| N-methyl-2-pyrrolidone | — | 20% | 5% |
| epoxidised coconut oil | — | — | 90% |

These solutions are suitable for application in the form of micro-drops.

| (c) Granulates | (a) | (b) |
|---|---|---|
| a compound according to Table 1 or 2 | 5% | 10% |
| kaolin | 94% | — |
| highly dispersed silicic acid | 1% | — |
| attapulgite | — | 90% |

The active ingredient is dissolved, sprayed onto the carrier, and the solvent is subsequently evaporated off in vacuo.

| (d) Dusts | (a) | (b) | (c) |
|---|---|---|---|
| a compound according to Table 1 or 2 | 2% | 5% | 8% |
| highly dispersed silicic acid | 1% | 5% | 5% |
| talcum | 97% | — | 10% |
| kaolin | — | 90% | 77% |

Ready-for-use dusts are obtained by homogeneously mixing the carriers with the active ingredient.

| (e) Wettable powders | (a) | (b) |
|---|---|---|
| a compound according Table 1 or 2 | 20% | 60% |
| sodium lignosulfonate | 5% | 5% |
| sodium lauryl sulfate | 3% | 6% |
| octylphenol polyethylene glycol ether (7–8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable powders which can be diluted with water to give suspensions of the desired concentration.

| (f) Extruder granulate | |
|---|---|
| a compound according to Table 1 or 2 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a steam of air.

| (g) Coated granulate | |
|---|---|
| a compound according to Table 1 or 2 | 3% |
| polyethylene glycol (MW 200) | 3% |
| kaolin | 94% |

The finely ground active ingredient is uniformly applied, in a mixer, to the kaolin moistened with polyethylene glycol. Non-dusty coated granulates are obtained in this manner.

| (h) Suspension concentrate | |
|---|---|
| a compound according to Table 1 or 2 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a | 75% |
| aqueous emulsion | 0.8% |
| water | 32% |

The finely ground active ingredient is intimately mixed with the adjuvants, giving a suspension concentrate from which suspensions of any desired concentration can be produced by dilution with water.

B. Biological Examples

Example B1

Pre-emergence herbicical action

In a greenhouse, immediately after sowing the test plants in seed trays the surface of the soil is treated with an aqueous dispersion of the test compound obtained from a 25% emulsifiable concentrate. Various rates of application of active ingredient/hectare are tested. The seed trays are kept in the greenhouse at 22°-25° C. and 50-70% relative humidity and the test is evaluated after 3 weeks.

The herbicidal action is assessed in comparison with an untreated control group using a nine-stage evaluation scale (1=total damage of the test plants, 9=no herbicidal action on the test plants).

Ratings of 1 to 4 (especially 1 to 3) indicate a good to very good herbicidal action. Ratings of 6 to 9 (especially 7 to 9) indicate a good tolerance (especially in the case of crop plants). The test results for compound No. 1.005 are compiled in Table 4.

TABLE 4

| Test plant | Rate of application [g/ha] | | | | | |
|---|---|---|---|---|---|---|
| | 2000 | 1000 | 5000 | 250 | 125 | 60 |
| barley | 7 | 7 | 9 | 9 | 9 | 9 |
| wheat | 8 | 9 | 9 | 9 | 9 | 9 |
| maize | 8 | 9 | 9 | 9 | 9 | 9 |
| sorghum | 7 | 8 | 9 | 9 | 9 | 9 |
| Abutilon | 1 | 1 | 2 | 2 | 2 | 5 |
| Chenopodium Sp. | 1 | 1 | 1 | 1 | 1 | 1 |
| Solanum nigrum | 1 | 1 | 1 | 1 | 2 | 3 |
| Veronica Sp. | 1 | 1 | 1 | 1 | 4 | 6 |

Example B2

Post-emergence herbicidal action

A number of weeds, both monocotyledons and dicotyledons, are sprayed after emergence (at the 4- to 6-leaf stage) with an aqueous dispersion of active ingredient at a rate of 250 g to 2 kg of active ingredient per hectare and kept at 24°-26° C. and 45-60% relative humidity. 15 days after the treatment the test is evaluated in accordance with the evaluation scheme described in Example B1.

The test results for compound 1.005 are compiled in Table 5.

TABLE 5

| Test plant | rate of application [g/ha] | | | |
|---|---|---|---|---|
| | 2000 | 1000 | 5000 | 250 |
| barley | 9 | 9 | 9 | 9 |
| wheat | 8 | 9 | 9 | 9 |
| maize | 8 | 9 | 9 | 9 |
| sorghum | 7 | 8 | 9 | 9 |
| rice (dry) | 7 | 8 | 9 | 9 |
| Abutilon | 1 | 1 | 2 | 3 |
| Chenopodium Sp. | 1 | 1 | 1 | 2 |
| Solanum nigrum | 1 | 1 | 1 | 2 |
| Sinapis | 2 | 2 | 3 | 3 |

Example B3

Herbicidal action in paddy

The water weeds Echinochloa crus galli and Monocharia vag. are sown in plastics beakers (60 cm² surface area, 500 ml volume). After sowing, the beakers are filled to the soil surface with water. 3 days after sowing, the water level is raised to slightly above (3-5 mm) the surface of the soil. Application is carried out 3 days after sowing by spraying an aqueous emulsion of the test substances onto the vessels at a rate of application of 60 to 250 g of active ingredient per hectare. The plant beakers are then placed in a greenhouse under optimum growth conditions for the rice weeds, i.e. at 25°-30° C. and high humidity. The tests are evaluated 3 weeks after the application. The compounds of Table 1 damage the weeds but not the rice.

I claim:

1. A compound of formula I or I'

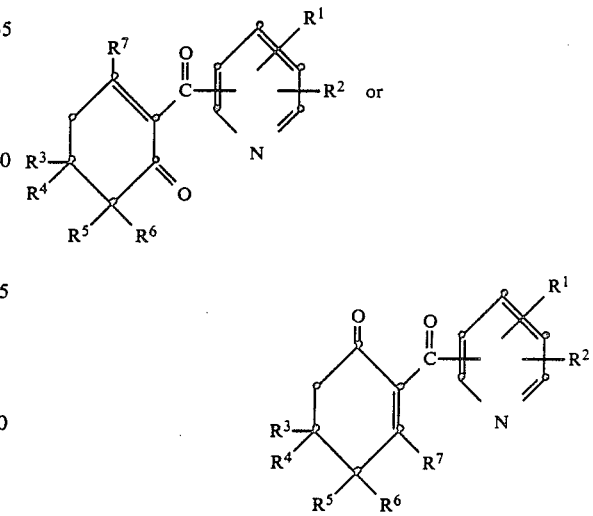

in which $R^1$ and $R^2$ independently of one another are each hydrogen; halogen; nitro; cyano; $C_1$-$C_4$alkyl; $C_1$-$C_4$alkoxy; $C_1$-$C_4$alkyl-S(O)$_n$—; COR$^8$; $C_1$-$C_4$haloalkoxy; or $C_1$-$C_4$haloalkyl; $R^3$, $R^4$ and $R^5$ independently of one another are each hydrogen; $C_1$-$C_4$alkyl; or phenyl or benzyl each unsubstituted or substituted by up to three identical or different substituents from halogen, nitro, cyano, $C_1$-$C_4$alkyl, $C_1$-$C_4$alkoxy, $C_1$-$C_4$alkyl-S(O)$_n$—, $C_1$-$C_4$haloalkyl, $C_1$-$C_4$haloalkyl-S(O)$_n$— and $C_1$-$C_4$haloalkoxy; $R^6$ is hydrogen; $C_1$-$C_4$alkyl; $C_1$-$C_4$alkoxycarbonyl; or cyano; $R^7$ is OH; or O$^\ominus$M$^\oplus$; $R^8$ is OH; $C_1$-$C_4$alkoxy; NH$_2$; $C_1$-$C_4$alkylamino; or di-$C_1$-$C_4$alkylamino; n is 0, 1 or 2; M$^\oplus$ is a cation equivalent of a metal ion or of an ammonium ion that is unsubstituted or substituted by up to three $C_1$-$C_4$alkyl, $C_1$-$C_4$hydroxyalkyl or $C_1$-$C_4$alkoxy-$C_1$-$C_4$alkyl groups.

2. A compound according to claim 1 of formula I or I'

[Structure I showing cyclohexanedione linked to pyridine ring with substituents $R^1$, $R^2$, $R^3$, $R^4$, $R^5$, $R^6$, $R^7$]

I

[Structure I' showing cyclohexanedione linked to pyridine ring with substituents $R^1$, $R^2$, $R^3$, $R^4$, $R^5$, $R^6$, $R^7$]

I' in which the radicals $R^1$ and $R^2$ are bonded in the 3- and 5-positions of the pyridine ring and the pyridinecarbonyl system is bonded by way of the 2-position of the pyridine ring.

3. A compound according to claim 1 of formula I or I'

[Structure I]

I

[Structure I']

I' in which $R^1$ is hydrogen; halogen; nitro; cyano; $C_1$-$C_4$alkyl; $C_1$-$C_4$alkoxy; $C_1$-$C_4$alkyl-S(O)$_n$—; $COR^8$; $C_1$-$C_4$haloalkoxy; or $C_1$-$C_4$haloalkyl; $R^2$ is hydrogen; halogen; nitro; cyano; $C_1$-$C_4$alkyl; $C_1$-$C_4$alkoxy; $C_1$-$C_4$haloalkoxy; $C_1$-$C_4$alkyl-S(O)$_n$—; or $C_1$-$C_4$haloalkyl; $R^3$, $R^4$ and $R^5$ independently of one another are each hydrogen; $C_1$-$C_4$alkyl; or phenyl or benzyl each unsubstituted or substituted by up to three identical or different substituents from halogen, nitro, cyano, $C_1$-$C_4$alkyl, $C_1$-$C_4$alkoxy, $C_1$-$C_4$alkyl-S(O)$_n$—, $C_1$-$C_4$haloalkyl, $C_1$-$C_4$haloalkyl-S(O)$_n$— and $C_1$-$C_4$haloalkoxy; $R^6$ is hydrogen; $C_1$-$C_4$alkoxycarbonyl; or cyano; $R^7$ is OH; or O$^{\ominus}$M$^{\oplus}$; $R^8$ is OH; $C_1$-$C_4$alkoxy; NH$_2$; $C_1$-$C_4$alkylamino; or di-$C_1$-$C_4$alkylamino; n is 0, 1 or 2; M$^{\oplus}$ is a cation equivalent of an alkali metal ion, an alkaline earth metal ion or an ammonium ion; of a mono-$C_1$-$C_4$alkylammonium ion; of a di-$C_1$-$C_4$alkylammonium ion; of a tri-$C_1$-$C_4$alkylammonium ion; or of a triethanolammonium ion.

4. A compound of formula I or I' in which at least one of the radicals $R^3$ to $R^6$ is hydrogen, according to claim 1.

5. A compound of formula I or I' in which at least two of the radicals $R^3$ to $R^6$ are hydrogen, according to claim 1.

6. A compound of formula I or I' in which $R^6$ is cyano and $R^5$ is hydrogen, according to claim 1.

7. A compound of formula I or I' in which $R^6$ is cyano, $R^6$ is hydrogen and $R^3$ and $R^4$ independently of one another are each hydrogen or $C_1$-$C_4$alkyl, according to claim 1.

8. A compound of formula I or I' in which $R^6$ is $C_1$-$C_4$alkoxycarbonyl, according to claim 1.

9. A compound of formula I or I' in which $R^7$ is OH, according to claim 1.

10. A compound of formula I or I' in which $R^7$ is O$^{\ominus}$—M$^{\oplus}$, according to claim 1.

11. A compound of formula I or I' in which $R^1$ is hydrogen, chlorine, fluorine, nitro, trifluoromethyl, methoxy, bromine, methylthio, methylsulfonyl, carboxy, trichloromethyl or methyl, according to claim 1.

12. Cyclohexanediones of formula I or I' in which $R^2$ is hydrogen, chlorine, nitro, methylthio, methylsulfinyl, methylsulfonyl, methyl, fluorine, trifluoromethyl or trichloromethyl, according to claim 1.

13. 2-(3-chloro-5-trifluoromethylpyridin-2-ylcarbonyl)-cyclohex-1-en-1-ol-3-one or 2-(3-chloro-b 5-methylsulfonylpyridin-2-ylcarbonyl)-cyclohex-1-en-1-ol-3-one as a compound of formula I according to claim 1.

14. A herbicidal composition which comprises a herbicidally effective amount of a compound of formula I or I' according to claim 1, together with a carrier or other adjuvant.

15. A method of controlling undesired plant growth, which comprises allowing a herbicidally effective amount of a compound of formula I or I' according to claim 1 to act on the plants to be controlled or the locus thereof.

* * * * *